(12) United States Patent
Smothers et al.

(10) Patent No.: US 7,237,556 B2
(45) Date of Patent: Jul. 3, 2007

(54) IMAGE-GUIDED FRACTURE REDUCTION

(75) Inventors: Crista Smothers, Cordova, TN (US); David Marc Kahler, Earlysville, VA (US); Lauralan Terrill-Grisoni, Cordova, TN (US); David Castleman, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 10/364,859

(22) Filed: Feb. 11, 2003

(65) Prior Publication Data

US 2003/0181918 A1 Sep. 25, 2003

Related U.S. Application Data

(60) Provisional application No. 60/355,886, filed on Feb. 11, 2002.

(51) Int. Cl.
*A61B 19/00* (2006.01)
*A61B 5/05* (2006.01)

(52) U.S. Cl. .................. 128/898; 606/130; 606/86; 600/427

(58) Field of Classification Search .................. 606/86, 606/97, 96, 130, 1; 128/898; 600/407, 426, 600/427, 429
See application file for complete search history.

(56) References Cited

U.S. PATENT DOCUMENTS

| 100,602 | A | 3/1870 | Coes |
|---|---|---|---|
| 1,076,971 | A | 10/1913 | Geiger |
| 1,201,467 | A | 10/1916 | Hoglund |
| 2,092,869 | A | 9/1937 | Baum |
| 3,412,733 | A | 11/1968 | Ross |
| 3,457,922 | A | 7/1969 | Ray |
| 3,702,611 | A | 11/1972 | Fishbein |
| 4,305,394 | A | 12/1981 | Bertuch, Jr. |
| 4,323,080 | A | 4/1982 | Melharty |
| 4,421,112 | A | 12/1983 | Mains et al. |
| 4,457,307 | A | 7/1984 | Stillwell |
| 4,483,554 | A | 11/1984 | Ernst |
| 4,524,766 | A | 6/1985 | Petersen |
| 4,534,364 | A | 8/1985 | Lamoreux |
| 4,565,192 | A | 1/1986 | Shapiro |
| 4,566,448 | A | 1/1986 | Rohr, Jr. |
| 4,567,885 | A | 2/1986 | Androphy |
| 4,567,886 | A | 2/1986 | Petersen |

(Continued)

FOREIGN PATENT DOCUMENTS

DE 42 25 112 C 12/1993

(Continued)

OTHER PUBLICATIONS

Patent Abstracts of Japan, vol. 2002, No. 05, May 3, 2002 & JP 2002 017740A (Ochi Takahiro; Yonenobu Sakuo: MMT:KK) Jan. 22, 2002 Abstract.

(Continued)

*Primary Examiner*—Pedro Philogene
(74) *Attorney, Agent, or Firm*—Kilpatrick Stockton LLP

(57) ABSTRACT

Embodiments of the present invention include products and methods for reducing fractures with the aid of image guidance. In one embodiment, products and methods are directed to reduction for the placement of an intramedullary nail.

45 Claims, 16 Drawing Sheets

U.S. PATENT DOCUMENTS

| | | |
|---|---|---|
| 4,574,794 A | 3/1986 | Cooke et al. |
| 4,583,554 A | 4/1986 | Mittelman et al. |
| 4,703,751 A | 11/1987 | Pohl |
| 4,712,951 A | 12/1987 | Brown |
| 4,718,413 A | 1/1988 | Johnson |
| 4,722,056 A | 1/1988 | Roberts et al. |
| 4,759,350 A | 7/1988 | Dunn et al. |
| 4,802,468 A | 2/1989 | Powlan |
| 4,803,976 A * | 2/1989 | Frigg et al. .................. 606/97 |
| 4,875,475 A | 10/1989 | Comte et al. |
| 4,892,093 A | 1/1990 | Zarnowski et al. |
| 4,913,163 A | 4/1990 | Roger et al. |
| 4,938,762 A | 7/1990 | Wehrli |
| 4,952,213 A | 8/1990 | Bowman et al. |
| 4,964,862 A | 10/1990 | Arms |
| 4,991,579 A | 2/1991 | Allen |
| 5,002,545 A | 3/1991 | Whiteside et al. |
| 5,016,639 A | 5/1991 | Allen |
| 5,037,423 A | 8/1991 | Kenna |
| 5,037,426 A | 8/1991 | Goble et al. |
| 5,049,149 A | 9/1991 | Schmidt |
| 5,053,039 A | 10/1991 | Hofmann et al. |
| 5,078,719 A | 1/1992 | Schreiber |
| 5,092,869 A | 3/1992 | Waldron |
| 5,094,241 A | 3/1992 | Allen |
| 5,097,839 A | 3/1992 | Allen |
| 5,116,338 A | 5/1992 | Poggie et al. |
| 5,119,817 A | 6/1992 | Allen |
| 5,122,144 A | 6/1992 | Bert et al. |
| 5,129,909 A | 7/1992 | Sutherland |
| 5,190,547 A | 3/1993 | Barber, Jr. et al. |
| 5,211,164 A | 5/1993 | Allen |
| 5,213,312 A | 5/1993 | MacDonald |
| 5,217,499 A | 6/1993 | Shelley |
| 5,246,444 A | 9/1993 | Schreiber |
| 5,254,119 A | 10/1993 | Schreiber |
| 5,289,826 A | 3/1994 | Kovacevic |
| 5,305,203 A | 4/1994 | Raab |
| 5,360,016 A | 11/1994 | Kovacevic |
| 5,364,401 A | 11/1994 | Ferrante et al. |
| 5,364,402 A | 11/1994 | Mumme et al. |
| 5,375,588 A | 12/1994 | Yoon |
| 5,379,133 A | 1/1995 | Kirk |
| 5,383,454 A | 1/1995 | Bucholz |
| 5,389,101 A | 2/1995 | Heilbrun et al. |
| 5,395,376 A | 3/1995 | Caspari et al. |
| 5,397,329 A | 3/1995 | Allen |
| 5,423,828 A | 6/1995 | Benson |
| 5,425,355 A | 6/1995 | Kulick |
| 5,445,166 A | 8/1995 | Taylor |
| 5,445,642 A | 8/1995 | McNulty et al. |
| 5,449,360 A | 9/1995 | Schreiber |
| 5,462,548 A | 10/1995 | Pappas et al. |
| 5,462,549 A | 10/1995 | Glock |
| 5,468,244 A | 11/1995 | Attfield et al. |
| 5,470,354 A | 11/1995 | Hershberger et al. |
| 5,474,559 A | 12/1995 | Bertin et al. |
| 5,486,178 A | 1/1996 | Hodge |
| 5,490,854 A | 2/1996 | Fisher et al. |
| 5,491,510 A | 2/1996 | Gove |
| 5,507,824 A | 4/1996 | Lennox |
| 5,514,139 A | 5/1996 | Goldstein et al. |
| 5,517,990 A | 5/1996 | Kalfas et al. |
| 5,540,691 A | 7/1996 | Elmstrom et al. |
| 5,540,695 A | 7/1996 | Levy |
| 5,540,696 A | 7/1996 | Booth, Jr. et al. |
| 5,569,260 A | 10/1996 | Petersen |
| 5,597,379 A | 1/1997 | Haines et al. |
| 5,598,269 A | 1/1997 | Kitaevich et al. |
| 5,603,318 A | 2/1997 | Heilbrun et al. |
| 5,613,969 A | 3/1997 | Jenkins, Jr. |
| 5,643,268 A | 7/1997 | Vilsmeier et al. |
| 5,643,272 A | 7/1997 | Haines et al. |
| 5,658,290 A | 8/1997 | Lechot |
| 5,669,914 A | 9/1997 | Eckhoff |
| 5,676,668 A | 10/1997 | McCue et al. |
| 5,682,886 A | 11/1997 | Delp et al. |
| 5,683,397 A | 11/1997 | Vendrely et al. |
| 5,688,279 A | 11/1997 | McNulty et al. |
| 5,693,056 A | 12/1997 | Carls et al. |
| 5,702,406 A | 12/1997 | Vilsmeier et al. |
| 5,704,941 A | 1/1998 | Jacober et al. |
| 5,709,689 A | 1/1998 | Ferrante et al. |
| 5,715,836 A | 2/1998 | Kliegis et al. |
| 5,716,361 A | 2/1998 | Masini |
| 5,720,752 A | 2/1998 | Elliott et al. |
| 5,722,978 A | 3/1998 | Jenkins, Jr. |
| 5,733,292 A | 3/1998 | Gustilo et al. |
| 5,735,904 A | 4/1998 | Pappas |
| 5,743,915 A | 4/1998 | Bertin et al. |
| 5,748,767 A | 5/1998 | Raab |
| 5,755,725 A | 5/1998 | Druais |
| 5,755,803 A | 5/1998 | Haines et al. |
| 5,769,861 A | 6/1998 | Vilsmeier |
| 5,772,593 A | 6/1998 | Hakamata |
| 5,772,594 A | 6/1998 | Barrick |
| 5,776,064 A | 7/1998 | Kalfas et al. |
| 5,782,842 A | 7/1998 | Kloess et al. |
| 5,792,147 A | 8/1998 | Evans et al. |
| 5,797,924 A | 8/1998 | Schulte et al. |
| 5,799,055 A | 8/1998 | Peshkin et al. |
| 5,800,352 A | 9/1998 | Ferre et al. |
| 5,800,438 A | 9/1998 | Tuke et al. |
| 5,807,252 A | 9/1998 | Hassfeld et al. |
| 5,810,827 A | 9/1998 | Haines et al. |
| 5,810,841 A | 9/1998 | McNeirney et al. |
| 5,817,097 A | 10/1998 | Howard et al. |
| 5,836,954 A | 11/1998 | Heilbrun et al. |
| 5,848,967 A | 12/1998 | Cosman |
| 5,850,836 A | 12/1998 | Steiger et al. |
| 5,860,981 A | 1/1999 | Bertin et al. |
| 5,865,809 A | 2/1999 | Moenning et al. |
| 5,871,018 A | 2/1999 | Delp et al. |
| 5,871,445 A | 2/1999 | Bucholz |
| 5,879,352 A | 3/1999 | Filoso et al. |
| 5,880,976 A | 3/1999 | DiGioia, III et al. |
| 5,885,296 A | 3/1999 | Masini |
| 5,885,297 A | 3/1999 | Matsen, III |
| 5,897,559 A | 4/1999 | Masinie |
| 5,916,221 A | 6/1999 | Hodorek et al. |
| 5,920,395 A | 7/1999 | Schulz |
| 5,921,992 A | 7/1999 | Costales et al. |
| 5,925,049 A | 7/1999 | Gustilo et al. |
| 5,935,128 A | 8/1999 | Carter et al. |
| 5,938,665 A | 8/1999 | Martin |
| 5,944,722 A | 8/1999 | Masini |
| 5,947,971 A | 9/1999 | Kuslich et al. |
| 5,947,973 A | 9/1999 | Masini |
| 5,951,561 A | 9/1999 | Pepper et al. |
| 5,957,926 A | 9/1999 | Masini |
| 5,961,523 A | 10/1999 | Masini |
| 5,971,989 A | 10/1999 | Masini |
| 5,980,526 A | 11/1999 | Johnson et al. |
| 5,980,535 A | 11/1999 | Barnett et al. |
| 5,999,837 A | 12/1999 | Messner et al. |
| 6,001,106 A | 12/1999 | Ryan et al. |
| 6,002,859 A | 12/1999 | DiGioia, III et al. |
| 6,006,126 A | 12/1999 | Cosman |
| 6,007,537 A | 12/1999 | Burkinshaw et al. |
| 6,010,506 A | 1/2000 | Gosney et al. |
| 6,011,987 A | 1/2000 | Barnett |
| 6,016,606 A | 1/2000 | Oliver et al. |
| 6,021,342 A | 2/2000 | Brabrand |
| 6,021,343 A | 2/2000 | Foley et al. |

| | | | |
|---|---|---|---|
| 6,022,377 A | 2/2000 | Nuelle et al. | |
| 6,026,315 A | 2/2000 | Lenz et al. | |
| 6,033,410 A | 3/2000 | McLean et al. | |
| 6,041,249 A | 3/2000 | Regn | |
| 6,044,291 A | 3/2000 | Rockseisen | |
| 6,050,724 A | 4/2000 | Schmitz et al. | |
| 6,053,922 A * | 4/2000 | Krause et al. | 606/80 |
| 6,056,756 A | 5/2000 | Eng et al. | |
| 6,068,633 A | 5/2000 | Masini | |
| 6,069,932 A | 5/2000 | Peshkin et al. | |
| 6,073,044 A | 6/2000 | Fitzpatrick et al. | |
| 6,077,269 A | 6/2000 | Masini | |
| 6,081,336 A | 6/2000 | Messner et al. | |
| 6,083,163 A | 7/2000 | Wegner et al. | |
| 6,102,916 A | 8/2000 | Masini | |
| 6,132,433 A | 10/2000 | Whelan | |
| 6,143,390 A | 11/2000 | Takamiya et al. | |
| 6,144,875 A | 11/2000 | Schweikard et al. | |
| 6,146,390 A | 11/2000 | Heilbrun et al. | |
| 6,148,280 A | 11/2000 | Kramer | |
| 6,161,033 A | 12/2000 | Kuhn | |
| 6,162,190 A | 12/2000 | Kramer | |
| 6,165,181 A | 12/2000 | Heilbrun et al. | |
| 6,167,145 A | 12/2000 | Foley et al. | |
| 6,167,292 A | 12/2000 | Badano et al. | |
| 6,167,295 A | 12/2000 | Cosman | |
| 6,167,296 A | 12/2000 | Shahidi | |
| 6,168,627 B1 | 1/2001 | Huebner | |
| 6,185,315 B1 | 2/2001 | Schmucker et al. | |
| 6,187,010 B1 | 2/2001 | Masini | |
| 6,190,320 B1 | 2/2001 | Lelong | |
| 6,190,395 B1 | 2/2001 | Williams | |
| 6,195,168 B1 | 2/2001 | De Lega et al. | |
| 6,197,064 B1 | 3/2001 | Haines et al. | |
| 6,198,794 B1 | 3/2001 | Peshkin et al. | |
| 6,200,316 B1 | 3/2001 | Zwirkoski et al. | |
| 6,205,411 B1 | 3/2001 | DiGioia, III et al. | |
| 6,211,976 B1 | 4/2001 | Popovich et al. | |
| 6,214,011 B1 | 4/2001 | Masini | |
| 6,216,029 B1 | 4/2001 | Paltieli | |
| 6,223,067 B1 | 4/2001 | Vilsmeier et al. | |
| 6,226,548 B1 | 5/2001 | Foley et al. | |
| 6,228,090 B1 | 5/2001 | Waddell | |
| 6,235,038 B1 * | 5/2001 | Hunter et al. | 606/130 |
| 6,236,875 B1 | 5/2001 | Bucholz et al. | |
| 6,241,735 B1 | 6/2001 | Marmulla | |
| 6,249,581 B1 | 6/2001 | Kok | |
| 6,258,095 B1 | 7/2001 | Lombardo et al. | |
| 6,258,096 B1 | 7/2001 | Seki | |
| 6,264,647 B1 | 7/2001 | Lechot | |
| 6,283,971 B1 | 9/2001 | Temeles | |
| 6,285,902 B1 | 9/2001 | Kienzle, III et al. | |
| 6,317,616 B1 | 11/2001 | Glossop | |
| 6,332,891 B1 | 12/2001 | Himes | |
| 6,333,971 B2 | 12/2001 | McCrory et al. | |
| 6,344,853 B1 | 2/2002 | Knight | |
| 6,347,240 B1 | 2/2002 | Foley et al. | |
| 6,351,659 B1 | 2/2002 | Vilsmeier | |
| 6,351,661 B1 | 2/2002 | Cosman | |
| 6,377,839 B1 | 4/2002 | Kalfas et al. | |
| 6,383,188 B2 | 5/2002 | Kuslich et al. | |
| 6,385,475 B1 | 5/2002 | Cinquin et al. | |
| 6,405,072 B1 | 6/2002 | Cosman | |
| 6,413,261 B1 | 7/2002 | Grundei | |
| 6,434,507 B1 | 8/2002 | Clayton et al. | |
| 6,440,140 B2 | 8/2002 | Bullivant et al. | |
| 6,451,059 B1 | 9/2002 | Janas et al. | |
| 6,458,135 B1 | 10/2002 | Harwin et al. | |
| 6,468,202 B1 | 10/2002 | Irion et al. | |
| 6,477,400 B1 * | 11/2002 | Barrick | 600/426 |
| 6,478,799 B1 | 11/2002 | Williamson | |
| 6,490,467 B1 | 12/2002 | Bucholz et al. | |
| 6,491,429 B1 | 12/2002 | Suhm | |
| 6,491,702 B2 | 12/2002 | Heilbrun et al. | |
| 6,503,249 B1 * | 1/2003 | Krause | 606/62 |
| 6,503,254 B2 | 1/2003 | Masini | |
| 6,527,443 B1 | 3/2003 | Vilsmeier et al. | |
| 6,540,739 B2 | 4/2003 | Lechot | |
| 6,546,279 B1 | 4/2003 | Bova et al. | |
| 6,551,319 B2 | 4/2003 | Lieberman | |
| 6,551,324 B2 | 4/2003 | Muller | |
| 6,551,325 B2 | 4/2003 | Neubauer et al. | |
| 6,554,837 B1 | 4/2003 | Hauri et al. | |
| 6,558,391 B2 | 5/2003 | Axelson, Jr. et al. | |
| 6,558,421 B1 | 5/2003 | Fell et al. | |
| 6,567,687 B2 | 5/2003 | Front et al. | |
| 6,574,493 B2 | 6/2003 | Rasche et al. | |
| 6,595,997 B2 | 7/2003 | Axelson, Jr. et al. | |
| 6,602,259 B1 | 8/2003 | Masini | |
| 6,620,168 B1 | 9/2003 | Lombardo et al. | |
| 6,620,268 B2 | 9/2003 | Cho et al. | |
| 6,640,127 B1 | 10/2003 | Kosaka et al. | |
| 6,652,142 B2 | 11/2003 | Launay et al. | |
| 6,662,036 B2 | 12/2003 | Cosman | |
| 6,673,077 B1 | 1/2004 | Katz | |
| 6,675,040 B1 | 1/2004 | Cosman | |
| 6,685,711 B2 | 2/2004 | Axelson, Jr. et al. | |
| 6,692,447 B1 | 2/2004 | Picard | |
| 6,695,848 B2 | 2/2004 | Haines | |
| 6,702,821 B2 | 3/2004 | Bonutti | |
| 6,711,431 B2 | 3/2004 | Sarin et al. | |
| 6,712,824 B2 | 3/2004 | Millard et al. | |
| 6,716,249 B2 | 4/2004 | Hyde | |
| 6,718,194 B2 * | 4/2004 | Kienzle, III | 600/424 |
| 6,725,082 B2 * | 4/2004 | Sati et al. | 600/429 |
| 6,728,599 B2 | 4/2004 | Wright et al. | |
| 6,780,190 B2 | 8/2004 | Maroney | |
| 6,785,593 B2 | 8/2004 | Wang | |
| 6,799,088 B2 | 9/2004 | Wang | |
| 6,827,723 B2 | 12/2004 | Carson | |
| 6,836,703 B2 | 12/2004 | Wang | |
| 6,871,117 B2 | 3/2005 | Wang | |
| 6,892,112 B2 | 5/2005 | Wang | |
| 6,993,374 B2 | 1/2006 | Sasso | |
| 2001/0001120 A1 | 5/2001 | Masini | |
| 2001/0014772 A1 | 8/2001 | Lampotang et al. | |
| 2001/0016745 A1 | 8/2001 | Bullivant et al. | |
| 2001/0034530 A1 | 10/2001 | Malackowski et al. | |
| 2001/0036245 A1 | 11/2001 | Kienzle, III et al. | |
| 2001/0039421 A1 | 11/2001 | Heilbrun et al. | |
| 2002/0002330 A1 | 1/2002 | Vilsmeier | |
| 2002/0002365 A1 | 1/2002 | Lechot | |
| 2002/0011594 A1 | 1/2002 | DeSouza | |
| 2002/0016540 A1 | 2/2002 | Mikus et al. | |
| 2002/0029041 A1 | 3/2002 | Hover et al. | |
| 2002/0032451 A1 | 3/2002 | Tierney et al. | |
| 2002/0038085 A1 | 3/2002 | Immerz | |
| 2002/0052606 A1 | 5/2002 | Bonutti | |
| 2002/0065461 A1 | 5/2002 | Cosman | |
| 2002/0068942 A1 | 6/2002 | Neubauer et al. | |
| 2002/0069591 A1 | 6/2002 | Yancey | |
| 2002/0072748 A1 | 6/2002 | Robioneck | |
| 2002/0077533 A1 | 6/2002 | Bieger et al. | |
| 2002/0077540 A1 | 6/2002 | Kienzle, III | |
| 2002/0085681 A1 | 7/2002 | Jensen | |
| 2002/0087101 A1 | 7/2002 | Barrick et al. | |
| 2002/0095081 A1 | 7/2002 | Vilsmeier | |
| 2002/0107518 A1 | 8/2002 | Neubauer et al. | |
| 2002/0115934 A1 | 8/2002 | Tuke | |
| 2002/0133161 A1 | 9/2002 | Axelson et al. | |
| 2002/0133175 A1 | 9/2002 | Carson | |
| 2002/0147455 A1 | 10/2002 | Carson | |
| 2002/0151898 A1 | 10/2002 | Sohngen et al. | |
| 2002/0156371 A1 | 10/2002 | Hedlund et al. | |
| 2002/0156479 A1 | 10/2002 | Schulzki et al. | |
| 2002/0188194 A1 | 12/2002 | Cosman | |

| | | | | | | |
|---|---|---|---|---|---|---|
| 2002/0193800 A1 | 12/2002 | Kienzle, III et al. | EP | 0 380 451 A2 | 8/1990 | |
| 2002/0198448 A1 | 12/2002 | Zuk et al. | EP | 0 415 837 A2 | 3/1991 | |
| 2002/0198451 A1 | 12/2002 | Carson | EP | 0 466 659 A2 | 1/1992 | |
| 2002/0198531 A1 | 12/2002 | Millard et al. | EP | 0 538 152 A1 | 4/1993 | |
| 2003/0018338 A1 | 1/2003 | Axelson, Jr. et al. | EP | 0 538 153 B1 | 4/1993 | |
| 2003/0045883 A1 | 3/2003 | Chow et al. | EP | 0 555 003 B1 | 8/1993 | |
| 2003/0153829 A1 | 8/2003 | Sarin et al. | EP | 0 676 178 A | 10/1995 | |
| 2003/0153859 A1 | 8/2003 | Hinshon | EP | 0 720 834 A2 | 7/1996 | |
| 2003/0153978 A1 | 8/2003 | Whiteside | EP | 1 149 562 A2 | 10/2001 | |
| 2003/0164172 A1 | 9/2003 | Chumas et al. | EP | 1 190 676 B1 | 3/2002 | |
| 2003/0181918 A1 | 9/2003 | Smothers et al. | EP | 1 226 788 A1 | 7/2002 | |
| 2003/0187351 A1 | 10/2003 | Franck et al. | EP | 1 236 450 A1 | 9/2002 | |
| 2003/0187452 A1 | 10/2003 | Smith et al. | EP | 1 249 207 | 10/2002 | |
| 2003/0192557 A1 | 10/2003 | Krag et al. | EP | 1 384 456 A2 | 1/2004 | |
| 2003/0225329 A1 | 12/2003 | Rossner et al. | EP | 1 405 603 A2 | 4/2004 | |
| 2004/0019382 A1 | 1/2004 | Amirouche et al. | EP | 1 435 223 A1 | 7/2004 | |
| 2004/0030237 A1 | 2/2004 | Lee et al. | EP | 1 442 715 | 8/2004 | |
| 2004/0030245 A1 | 2/2004 | Noble et al. | EP | 1 459 686 A2 | 9/2004 | |
| 2004/0054489 A1 | 3/2004 | De La Barrera | EP | 1 532 946 A2 | 5/2005 | |
| 2004/0073279 A1 | 4/2004 | Malackowski et al. | GB | 2 224 937 | 5/1990 | |
| 2004/0087852 A1 | 5/2004 | Chen et al. | GB | 2 397 769 A | 8/2004 | |
| 2004/0097952 A1 | 5/2004 | Sarin et al. | WO | WO 1986/05384 | 9/1986 | |
| 2004/0167391 A1 | 8/2004 | Solar et al. | WO | WO 1989/09570 | 10/1989 | |
| 2004/0254586 A1 | 12/2004 | Sarin | WO | WO 94/17733 | 8/1994 | |
| 2004/0260290 A1 | 12/2004 | Zander et al. | WO | WO 95/15714 | 6/1995 | |
| 2005/0021037 A1 | 1/2005 | McCombs et al. | WO | WO 96/35387 | 11/1996 | |
| 2005/0021043 A1 | 1/2005 | Jansen | WO | WO 97/16129 | 5/1997 | |
| 2005/0075632 A1 | 4/2005 | Russell et al. | WO | WO 97/23172 | 7/1997 | |
| 2005/0085822 A1 | 4/2005 | Thornberry et al. | WO | WO 97/29683 | 8/1997 | |
| 2005/0109855 A1 | 5/2005 | McCombs | WO | WO 98/29032 | 7/1998 | |
| 2005/0113658 A1 | 5/2005 | Jacobson et al. | WO | WO 98/46169 | 10/1998 | |
| 2005/0113659 A1 | 5/2005 | Pothier | WO | WO 99/15097 | 4/1999 | |
| 2005/0113846 A1 | 5/2005 | Carson | WO | WO 99/27860 | 6/1999 | |
| 2005/0119639 A1 | 6/2005 | McCombs | WO | WO 99/60939 | 12/1999 | |
| 2005/0124988 A1 | 6/2005 | Terrill-Grisoni et al. | WO | WO 99/65380 | 12/1999 | |
| 2005/0148843 A1 | 7/2005 | Roose | WO | WO 00/00093 | 1/2000 | |
| 2005/0149003 A1 | 7/2005 | Tiemey et al. | WO | WO 00/21442 | 4/2000 | |
| 2005/0149041 A1 | 7/2005 | McGinley | WO | WO 00/47103 | * 8/2000 | ................. 606/130 |
| 2005/0159759 A1 | 7/2005 | Harbaugh et al. | WO | WO 00/64367 | 11/2000 | |
| 2005/0177172 A1 | 8/2005 | Acker | WO | WO 01/01845 A2 | 1/2001 | |
| 2005/0197569 A1 | 9/2005 | McCombs | WO | WO 01/19271 A2 | 3/2001 | |
| 2005/0228266 A1 | 10/2005 | McCombs | WO | WO 2001/34050 A2 | 5/2001 | |
| 2005/0228404 A1 | 10/2005 | Vandevelde | WO | WO 2001/34050 A3 | 5/2001 | |
| 2005/0234332 A1 | 10/2005 | Murphy | WO | WO 01/64124 1 A | 9/2001 | |
| 2005/0234465 A1 | 10/2005 | McCombs | WO | WO 01/67979 A1 | 9/2001 | |
| 2005/0234466 A1 | 10/2005 | Stallings | WO | WO 01/91647 A1 | 12/2001 | |
| 2005/0234468 A1 | 10/2005 | Carson | WO | WO 01/93770 A1 | 12/2001 | |
| 2005/0245808 A1 | 11/2005 | Carson | WO | WO 02/24096 A1 | 3/2002 | |
| 2005/0279368 A1 | 12/2005 | McCombs | WO | WO 02/041794 A1 | 5/2002 | |
| | | | WO | WO 02/063236 A1 | 8/2002 | |
| | FOREIGN PATENT DOCUMENTS | | WO | WO 02/063236 A3 | 8/2002 | |
| DE | 4225112 | 12/1993 | WO | WO 02/064042 | 8/2002 | |
| DE | 296 00 990 | 1/1996 | WO | WO 02/067783 | 9/2002 | |
| DE | 196 29 011 A1 | 1/1998 | WO | WO 02/067784 | 9/2002 | |
| DE | 197 09 960 A | 9/1998 | WO | WO 02/067800 | 9/2002 | |
| DE | 299 06 438 U1 | 9/1999 | WO | WO 02/080824 A1 | 10/2002 | |
| DE | 296 23 941 U1 | 11/2000 | WO | WO 2003/034213 A2 | 4/2003 | |
| DE | 200 21 494 | 3/2001 | WO | WO 03/034933 A2 | 5/2003 | |
| DE | 201 03 416 U1 | 7/2001 | WO | WO 03/039377 | 5/2003 | |
| DE | 100 12 042 | 8/2001 | WO | WO 03/041566 A2 | 5/2003 | |
| DE | 100 31 887 A1 | 1/2002 | WO | WO 2003/037192 A1 | 5/2003 | |
| DE | 102 07 035 | 2/2002 | WO | WO 03/065949 A2 | 8/2003 | |
| DE | 100 45 381 A1 | 4/2002 | WO | WO 03/068090 A1 | 8/2003 | |
| DE | 202 13 243 | 10/2002 | WO | WO 03/075740 A2 | 9/2003 | |
| DE | 203 09 399 | 8/2003 | WO | WO 2003/071969 A1 | 9/2003 | |
| EP | 0 327 509 A1 | 8/1989 | WO | WO 03/079940 | 10/2003 | |
| EP | 0 327 509 B1 | 8/1989 | WO | WO 03/096870 A2 | 11/2003 | |
| EP | 0 337 901 A1 | 10/1989 | WO | WO 2004/001569 A2 | 12/2003 | |
| EP | 0 340 176 A2 | 11/1989 | WO | WO 2004/017842 A2 | 3/2004 | |
| EP | 0 216 794 B1 | 12/1989 | WO | WO 204/029908 A1 | 4/2004 | |
| EP | 0 366 488 B1 | 5/1990 | WO | WO 204/030556 A2 | 4/2004 | |
| EP | 0 376 657 B1 | 7/1990 | WO | WO 2004/030559 A1 | 4/2004 | |
| | | | WO | WO 2004/046754 A2 | 6/2004 | |

| | | |
|---|---|---|
| WO | WI 2004/084740 A1 | 10/2004 |
| WO | WO 2004/084740 | 10/2004 |
| WO | WO2005/009303 A1 | 2/2005 |
| WO | WO 2005/039430 A2 | 5/2005 |
| WO | WO 2005/041802 A1 | 5/2005 |
| WO | WO 2005/044126 A1 | 5/2005 |
| WO | WO05/048851 A1 | 6/2005 |
| WO | WO05/053559 A1 | 6/2005 |
| WO | WO05/070312 A1 | 8/2005 |
| WO | WO 2005/070319 A1 | 8/2005 |
| WO | WO 2005/072629 A1 | 8/2005 |
| WO | WO 2005/096982 | 10/2005 |
| WO | WO 2005/104977 | 11/2005 |
| WO | WO 2005/104978 | 11/2005 |
| WO | WO 2006/044367 A1 | 4/2006 |
| WO | WO 2006/060631 A1 | 6/2006 |

OTHER PUBLICATIONS iON™ Smith & Nephew Orthopaedics Brochure entitled "You'll Never Look At Your Patients The Same Way Again." 10 pages (Jan. 2001).

International Search Report in related Application No. PCT/US03/04268.

Smith & Nephew—Orthopaedics—TriGen Reducer http://www.smithnephew.com/US/Standard.asp?NodeID=2996, one page (Jan. 21, 2003).

Smith & Nephew—Orthopaedics—TriGen Flexible Reamer System http://www.smithnephew.com/US/Standard.asp?NodeID=2998, 02 pages (Jan. 21. 2003).

Barnes, et al., "Unicompartmental Knee Arthroplasty," *Bombay Hospital Journal*, Issue Special, pp. 1-5, www.bhj.org/journal/1996/3803_july/special_486.htm.

Bonutti, et al., "Minimal Incision Total Knee Arthroplasty Using the Suspended Leg Technique," *Orthopedics*, (published Sep. 2003), 6 pages http://www.orthobluejournal.com/0903/9tips.asp.

Croitoru, et al., "Fixation-Based Surgery: A New Technique for Distal Radius Osteotomy," *Clinical Paper, Computer Aided Surgery* 2001, 160-169, vol. 6 (2001).

Delp, et al., "Computer-Assisted Knee Replacement," *Clinical Orthopaedics and Related Research*, 354:49-56 (1998).

Deluzio, et al., "Static alignment and the adduction moment in unicompartmental arthroplasty patients," Presented at NACOB 98: North American Congress on Biomechanics, University of Waterloo, Ontario, Canada, Aug. 14-18, 1998.

DiGioia, et al., "Computer Assisted Orthopedic Surgery," *Clinical Orthopaedics and Related Research*, Sep. 1998, vol. 354, pp. 8-16.

Ellis, et al., "A Surgical Planning and Guidance System for High Tibial Osteotomy," *Journal of Computer-Assisted Surgery*, 4(5):264-274 (1999).

Foley, et al., "Percutaneous pedicle screw fixation of the lumbar spine," *Neurosurg. Focus*, vol. 10(4), pp. 1-8 (2001).

Glossop, http:/www/traxta.com/papers/cua/mode1.html, 8 pages (Feb. 6, 2002).

Iyun, et al., "Planning and Performing the Ilizarov Method with the Taylor Spatial Frame," Abstract, at 2nd Annual Meeting of International Society for Computer Assisted Orthopaedic Surgery, Jun. 21, 2002, pp. 145-147.

Kanade, et al., "Image-Based Computer Assisted Orthopedic Surgery System," Bonecraft, Inc., 12 pages, Apr. 30, 2001.

Kiefer, et al., "Computer Aided Knee Arthroplasty Versus Conventional Technique—First Results," First Annual Meeting of the International Society for Computer Assisted Orthopedic Surgery, Davos, Switzerland, Feb. 8-10, 2001.

Kunz, et al., "Development and Verification of a Non-CT Based Total Knee Arthroplasty System for the LCS Prosthesis," First Annual Meeting of the International Society for Computer Assisted Orthopedic Surgery, Davos, Switzerland, Feb. 8-10, 2001.

Munoz, et al., "Computer Assisted Planning of Hig Tibial Osteotomy for the Treatment of Knee Osteoarthritis," http://www.utc.fr/esb/esb09/abs_htm/570.html (Feb. 21, 2002) (three pages).

Picard, et al., "Kneenav.TKR: Concept and Clinical Application," Computer Assisted Orthopedic Surgery USA 2000 Meeting, Pittsburgh, PA., Jun. 15-17, 2000.

Saragaglia, et al., "Computer Assisted Total Knee Arthroplasty: Comparison with a Conventional Procedure. Results of a 50 Cases Prospective Randomized Study," First Annual Meeting of the International Society for Computer Assisted Orthopedic Surgery, Davos, Switzerland, Feb. 8-10, 2001.

Simon, et al., "The Fundamentals of Virtual Fluoroscopy," Medtronic Surgical Navigation Technologies, Medtronic, pp. 57-66, Computer Assisted Orthopedic Surgery USA 2000 Meeting, Pittsburgh, PA, Jun. 15-17, 2000.

Sugano, et al., "Medical Robotics and Computer-Assisted Surgery in the Surgical Treatment of Patients and Rheumatic Diseases," *Cutting Edge Reports*, http://www/rheuma21st.com/archives/cutting_edge_Robotics_Japan. html (Apr. 27, 2000).

Suhm, et al., "Adapting the C-Arm Fluoroscope for Image Guided Orthopaedic Surgery," *CAOS*, pp. 212-214 (2002).

Tenbusch, et al., "First Results Using the Robodoc® System for Total Knee Replacement," First Annual Meeting of the International Society for Computer Assisted Orthopedic Surgery, Davos, Switzerland, Feb. 8-10, 2001.

Valstar, et al., "Towards computer-assisted surgery in should joint replacement," *ISPRS Journal of Photogrammetry & Remote Sensing*,56:326-337 (2002).

Stryker Navigation System brochure entitled " . . . best alignment for gap kinematics," 6 pages (2001).

BrainLAB Brochure entitled "Ortho . . . Your Partner for the Future" pp. 1-28 (2002).

Search Evolution Total Knee System—Relax—B. Braun Melsungen AG website http://www.orthopilot.com/index.cfm?uuid=26EA6AA4838D495B8A895420A83BD099&obj (3 pages, Sep. 2, 2003).

AO Development Institute "MEPUC Motorized Exact Positioning Unit . . . " one page (Mar. 26, 2003) http://www/ao-asif.ch/development/adi/examples/mepuc.shtml.

AO Development Institute "MEPUC Motorized Exact Positioning Unit for C-arm," one page (Jul. 7, 2003) http://www.ao-asif.ch/development/adi/examples/mepuc.shtml.

Smith & Nephew—Orthopaedics—CAS—Knees Computer Assisted Total Knee Replacement Surgery, 02 pages (Oct. 13, 2004) http://ortho.smith-nephew.com/us/Standard.asp?NodeId=3396.

Smith & Nephew Brochure entitled "Surgical Technique Mini Incision Hip Posterior Approach," 20 pages (Mar. 2003).

Smith & Nephew Richards Genesis® Total Knee System, "Revision Posterior Referencing Instrumentaion Surgical Technique," Brochure, pp. 1-51 (Dec. 1993).

Smith & Nephew Richards Genesis® "Total Knee System Primary Surgical Technique Anterior Referencing Instrumentation," pp. 59 (Dec. 1993).

Smith & Nephew Genesis II "Total Knee System Primary Surgical Technique," Brochure, pp. 1-36 (Mar. 2001).

National Institute of Arthritis and Musculoskeletal and Skin Diseases (NIAMS), "Questions & Answers about . . . Knee Problems", 36 pp. (May 2001).

Smith & Nephew Total Hip Replacement Surgery, HipReplacementInfo.com, 3 pages, Nov. 8, 2005 http://www/hipreplacementinfo.com/hip-total-replacement.htm.

Smith & Nephew Brochure, Design Features, "Opera" pp. 4-15 (1999).

Corinth Surgeon Performs Revolutionary Hip Replacement, Mississippi Medical News, pp. 1-2 (Nov. 17, 2005) http://host1.bondware.com/~mississippi/news.php?viewStory=347.

Dario, et al., 'Smart Surgical Tools and Augmenting Devices,' IEEE Trans. Rob. Autom., 19(5):782-792 (2003).

Fernandez-Lozano, et al., 'Human-machine interface evaluation in a computer assisted surgical system,' Proc. IEEE Int. Conf. Rob. Autom., 2004:231-236 (2004).

Martelli, et al., 'Criteria of interface evaluation for computer assisted surgery systems.' Int. J. Med. Informatics, 72:35-45 (2003).

Visarius, et al., 'Man-machine Interfaces in computer assisted surgery,' Computer Aided Surgery, pp. 102-107 (2004).

* cited by examiner

IMAGE-GUIDED FRACTURE REDUCTION

CROSS-REFERENCE TO RELATED APPLICATION

This application claims priority to U.S. Provisional Application No. 60/355,886 entitled "Image-Guided Fracture Reduction" filed on Feb. 11, 2002, the contents of which are incorporated herein by reference.

TECHNICAL FIELD

The invention is directed to treating skeletal fractures. More specifically, products and methods for reducing fractures with the aid of image guidance are disclosed.

BACKGROUND OF THE INVENTION

Fracture fixation of long bones such as the femur, tibia, humerus, fibula, or other long bones is challenging because of the difficulty of properly aligning and then securing fractured bone segments in place to allow the bone to heal. One very effective means of securing such fractures is intramedullary nailing. Intramedullary nailing is well-known in the art and essentially entails aligning two or more segments of bone that result from a fracture about a rod or nail that fits down the medullary canal of the fractured bone. Various techniques for intramedullary nailing are discussed in U.S. Pats. Nos. 5,951,561 and 6,010,506, which are hereby incorporated by reference.

Whether fixation is by intramedullary nailing or by some other means, the repositioning of the segments of a long bone fracture (fracture reduction) is one of the most challenging aspects of fracture fixation. The contraction of soft tissue subsequent to a fracture tends to shorten the fractured limb and place the fractured segments of the bone out of alignment relative to each other. Repositioning these segments to restore anatomic alignment can be very challenging.

One technique for realigning fractured bones comprises the use of a fracture table to first distract a limb back to its original length. When a patient is positioned and secured on the fracture table, a surgeon may then manipulate segments laterally to realign the segments. However, fracture tables are expensive and many surgeons do not use them due to cost, availability, or the limitations of having a patient fixed in one position. Multiple intra-operative x-ray or fluoroscopic images may need to be taken to assure alignment of the segments in all planes. Additionally, a fracture may continue to shift out of alignment as fixation is applied.

Another method for fracture reduction includes the attachment of an external distraction device to the bone via bone pins that pass through soft tissue and attach to the bone. These types of devices allow a surgeon to turn a threaded knob or other actuator and pull a fracture apart. Once distracted, repositioning is then accomplished by manual, physical manipulation of the limb. Once again, multiple intra-operative x-ray or fluoroscopic images may be necessary to assure proper realignment of the segments, and segments may shift out of alignment as fixation is applied.

Another method for fracture repositioning or reduction is through the use of the Internal Fracture Reduction Device manufactured by Smith & Nephew, Inc. This device is inserted into a portion of the fractured long bone and allows manipulation of a segment of the fractured bone. However, such a device must be inserted over a guide rod that has already been placed through the medullary canal of all fractured bone segments. Therefore, placement of the guide rod first requires at least adequate fracture alignment to place the guide rod through the realigned medullary canal.

Smith & Nephew, Inc. also manufactures a reducer for use with its TRIGEN® brand intramedullary nailing system. As shown in FIG. 1, the reducer 100 is an elongated, cannulated tube 101 with a connector 102 for attaching a handle 103. The inner diameter of the tube 101 is large enough to accommodate the passage of a guide rod (not shown). The outer diameter of the tube 101 is small enough to be inserted into a long bone without reaming the bone. The tube 101 is typically formed to the same shape as the intramedullary nail that will subsequently be implanted in the bone. The distal tip of the tube 101 includes a finger 104 that is bent up slightly. This finger 104 serves several purposes.

First, the finger 104 can be used to deflect a guide rod as the end of the guide rod passes the end of the tube 101. Specifically, the guide rod may be deflected in a desired direction by rotating the reducer 100 such that the distal end of the finger 104 is pointed in the desired direction. Second, the finger 104 places resistance on a guide rod that passes into or through the finger 104, thereby holding the guide rod in position relative to the reducer 100 by friction. Third, the curved tip of the finger 104 allows the reducer 100 to be pushed smoothly through the medullary canal of a proximal segment and into a distal segment. While the TRIGEN® system reducer has significant advantages, multiple intra-operative x-ray, fluoroscopic, or other such images must still be used to assure proper alignment of the segments in all planes as the reducer 100 is inserted.

Several manufactures currently produce image-guided surgical navigation systems that are used to assist in performing surgical procedures. The TREON™ and iON™ systems with FLUORONAV™ software manufactured by Medtronic Surgical Navigation Technologies, Inc. are examples of such systems. Systems and methods for accomplishing image-guided surgery are also disclosed in U.S. S No. 60/271,818 filed Feb. 27, 2001, entitled Image Guided System for Arthroplasty, which is incorporated herein by reference as are all documents incorporated by reference therein. Further image-guided surgery devices, systems, and methods are disclosed in a provisional application entitled SURGICAL NAVIGATION SYSTEMS AND PROCESSES, Application Serial No. 60/355,899, filed on Feb. 11, 2002, hereby incorporated by this reference.

The Medtronic systems use fluoroscopic imaging to capture anatomical characteristics and infrared cameras that detect certain targets placed in the surgical field to track instruments and anatomy. As used herein, an infrared camera can be any type of sensor or detector that is capable of sensing or detecting light of an infrared wavelength. Any number and orientation of so-called targets, fiducials, frames, markers, indicia, or any other desired location-assisting functionality ("references") can be used as targets to be detected by an imaging system or sensor. Other imaging or data capture systems such as CT, MRI, visual, sonic, digitized modeling, traditional x-ray equipment, or any other effective system or technique which has the capacity to image bone or other desired structures or tissue in the body can be used. Such systems generally include transducer functionality for emitting energy or otherwise performing sensing or location of objects and anatomical structure, a processor, mass memory storage, input/output functionality to control and direct operation of the system, and at least one monitor or other visual output functionality for rendering images that may be constructed by the system, whether or not in combination with images obtained from the transducer in real time.

Such systems typically combine processes and functionality for obtaining, storing, manipulating and rendering images of internal body structure with functionality that senses, stores, manipulates and virtually renders representations of components or objects such as instrumentation, trial components, surgical tools and other objects. The systems can then generate and display representations of the objects in combination with images of the body structure or tissue. Such combination renderings can be created using real time imaging of the body structure or tissue, or the system can obtain appropriate imaging of such structure or tissue and later computer generate and display renderings of it. The Medtronic systems, for instance, require the use of references attached to the anatomy, typically in a rigid fashion, such as to bone structure. The system tracks movement of the reference in three dimensions and then generates images of the bone structure's corresponding motion and location.

The references on the anatomy and the instruments either emit or reflect infrared light that is then detected by an infrared camera. The references may be sensed actively or passively by infrared, visual, sound, magnetic, electromagnetic, x-ray, or any other desired technique. An active reference emits energy, and a passive reference merely reflects energy. In some embodiments, the references have at least three, but usually four, markers that are tracked by an infrared sensor to determine the orientation of the reference and thus the geometry of the instrument, implant component or other object to which the reference is attached. References have been attached to surgical and implant devices such as instrumentation, trial instruments, and the like. For example, references have been attached to probes, instruments for placing acetabular cups and trial implants, drill guides, and cutting blocks.

The Medtronic imaging systems allow references to be detected at the same time the fluoroscopy imaging is occurring. Therefore, the position and orientation of the references may be coordinated with the fluoroscope imaging. Then, after processing position and orientation data, the references may be used to track the position and orientation of anatomical features that were recorded fluoroscopically. Computer-generated images of instrumentation, components, or other structures that are fitted with references may be superimposed on the fluoroscopic images. The instrumentation, trial, implant or other structure or geometry can be displayed as 3-D models, outline models, or bone-implant interface surfaces.

Current systems and techniques do not provide for effective image-guided reduction of fractures. Improved products and methods would include structures and techniques for guiding a reducer through the medullary canals of two or more bone segments that have been created by a fracture of a bone. Improved products and methods would also provide for reduced numbers of x-ray, fluoroscopic, or other images, and would not necessitate pre-operative imaging or surgical procedures prior to the primary procedure. Further, improved products and methods would allow alignment of bone segments to occur using images of at least one of the bone segments in combination with images of one or more implements, instruments, trials, guide wires, nails, reducers and other surgically related items, which are properly positioned and oriented in the images relative to the bone segments. Further, improved products and methods would provide for updated monitoring of bone segment positions, and therefore, rapid alignment of bone segments.

SUMMARY

An embodiment according to certain aspects of the invention is a method of aligning segments of a fractured bone. The method involves attaching references to at least two segments of a fractured bone and to a reducer. The position and orientation of at least two of the references are recorded, and the position and orientation of one or more of the segments of the fractured bone and in some embodiments, the reducer, are recorded. Each of the respective segments or reducer is located relative to a respective reference. The reducer is inserted into a medullary canal of one of the segments, and the reducer is aligned with a representation of another of the segments. The reducer is then inserted into a medullary canal of that segment.

Another embodiment according to certain aspects of the invention is a method of enabling reduction of a fractured bone by virtually representing at least one fractured segment of the bone and virtually representing an instrument for aligning two or more segments. The position and orientation of a first segment of the bone is recorded and that first segment is tracked. The position and orientation of the instrument for aligning the segments is recorded and tracked as well. If alignment has been achieved such that the instrument may be engaged with the first segment and a second segment, an indication is provided to a user through a virtual representation.

Still another embodiment according to certain aspects of the invention is an instrument operable with an image-guided surgical navigation system for aligning fractured segments of a bone. The instrument may include at least an elongated body and a reference coupled to the elongated body for enabling the instrument to be located by the image-guided surgical navigation system. The reference may have a predefined physical relationship with the elongated body such that by observing the position and orientation of the reference relative to at least one of the fractured segments, the position and orientation of the elongated body relative to at least one of the fractured segments can be determined.

Yet another embodiment according to certain aspects of the invention is a system for enabling reduction of a fractured bone. The system is operable to virtually represent at least one fractured segment of the bone and virtually represent an instrument for aligning the at least one fractured segment. The system includes a first reference coupled to the at least one fractured segment, and a second reference coupled to the instrument. This embodiment includes a detector operable to collect position and orientation information regarding the at least one fractured segment and the instrument, and a data processing device operable to store position and orientation information about the at least one fractured segment and the instrument, and to calculate virtual positions of the at least one fractured segment and the instrument based upon inputs from the detector. An indicator device for notifying a user of the relative positions of the at least one fractured segment and the instrument is also provided.

Yet a further embodiment according to certain aspects of the invention includes methods, instruments, and systems as described above, wherein the instrument enabling reduction or alignment of a fractured bone is a flexible reducer. The flexible reducer may be an elongated body with an at least partially flexible portion having one or more location elements associated with the flexible body. The one or more location elements can be provided on the flexible portion in order to assist determining the physical relationship of at least certain parts of the flexible portion with respect to a reference, a bone segment, or the surgical table. The at least partially flexible portion may further be provided with a feature or features that impart at least partial rigidity to the reducer.

DETAILED DESCRIPTION

Figure 1:
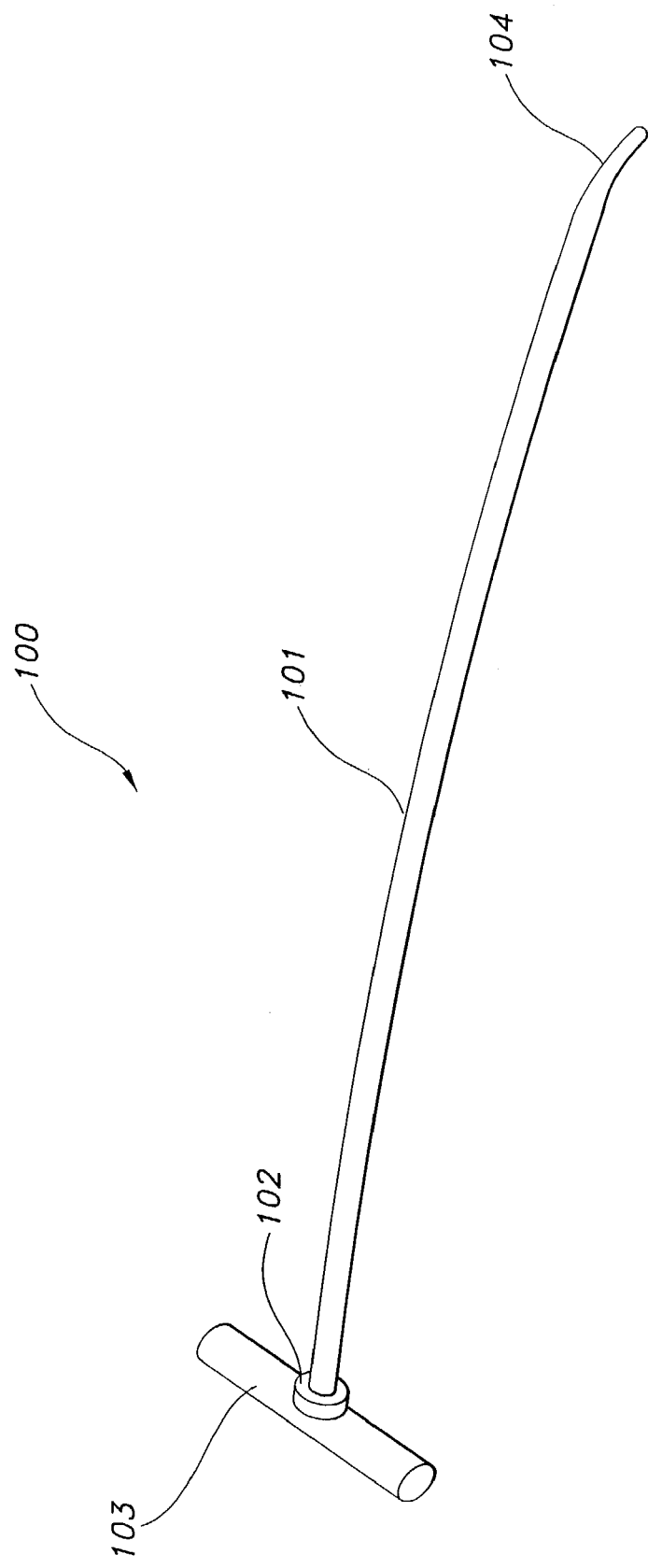
FIG. 1 is a perspective view of a prior art reducer.
Figure 2:
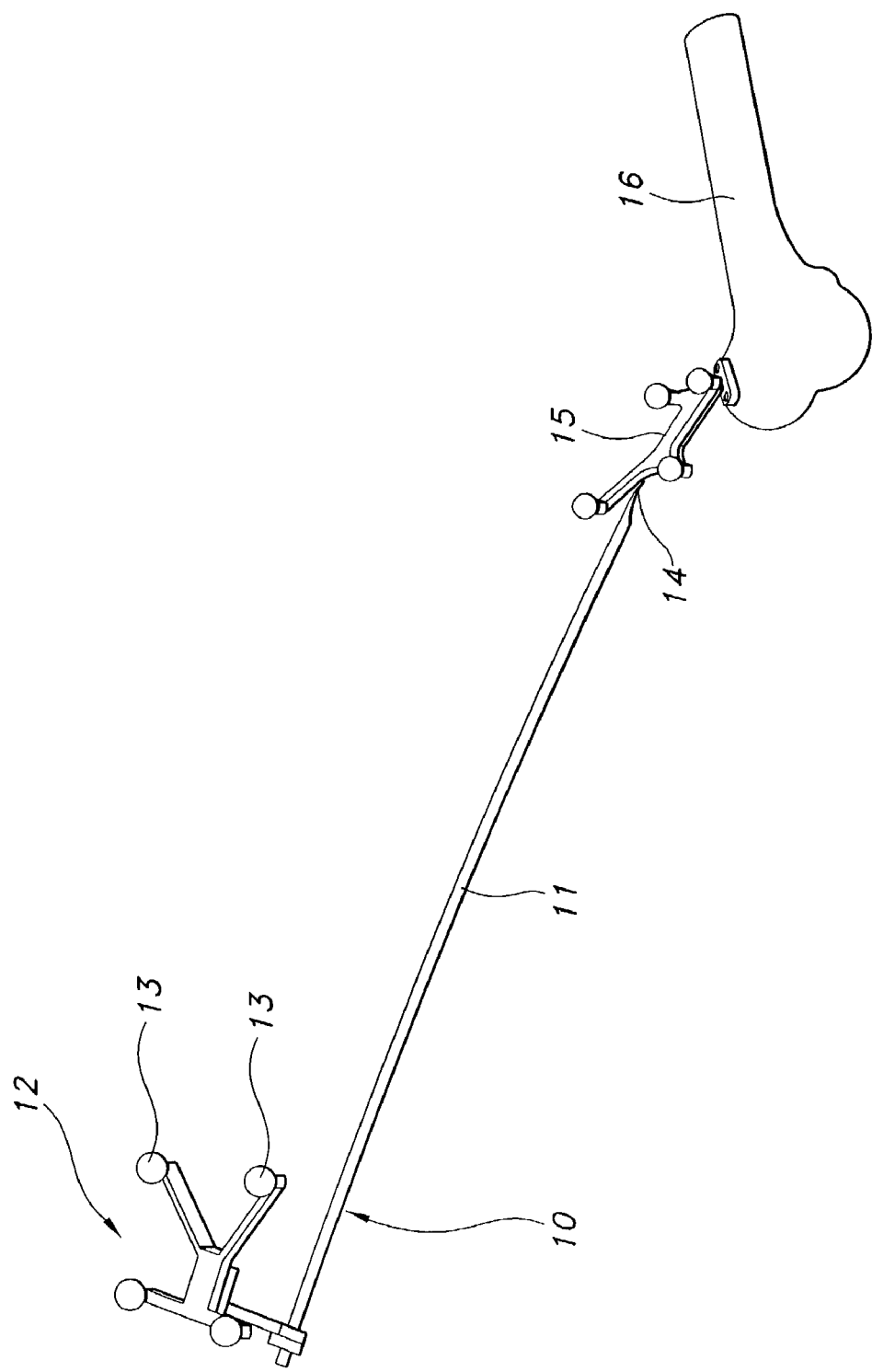
FIG. 2 is a perspective view of an embodiment of a navigated reducer and a segment of bone with an attached reference according to certain aspects of the invention.

FIG. 2 shows an instrument 10 according to certain aspects of the invention operable with an image-guided surgical navigation system. As described above, an image-guided surgical navigation system can be any of a variety of systems that capture anatomical characteristics and/or other references connected to the body and/or other surgical devices and/or other structures associated with a reference. Such a system then tracks parts of the body and the surgical devices relative to one another. Generally, reference to a system as "image-guided" means that the system produces images by which surgical navigation information is conveyed to the user. For example, a computer display showing virtual representations of an instrument and its relationship with a bone is considered one example of an image-guided system. As shown in FIG. 2, the position and orientation of instrument 10 are being recorded by placing finger 14 on a portion of a bone reference 15. As shown, the bone reference 15 is connected to an upper proportion 16 of a femur. The instrument 10 may be used to align fractured segments of a bone such as the upper portion 16 of a femur and a lower portion 20 of the femur shown in FIG. 3.

Figure 3:
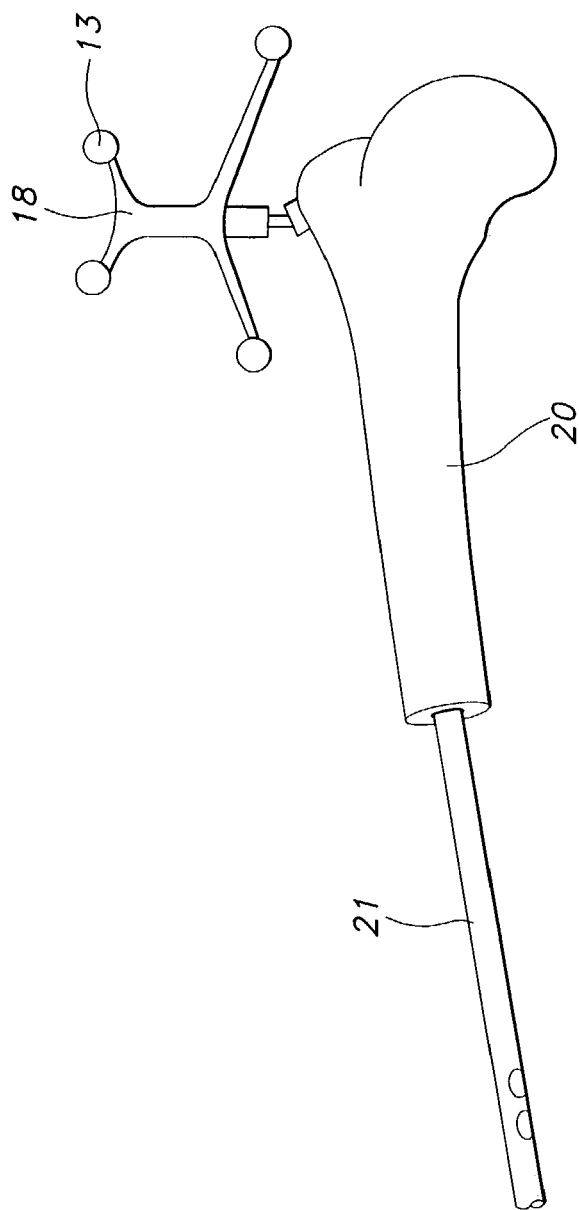
FIG. 3 is a perspective view of a segment of bone with an attached reference according to certain aspects of the invention, where the segment of bone contains an intramedullary nail.
Figures 4, 5:
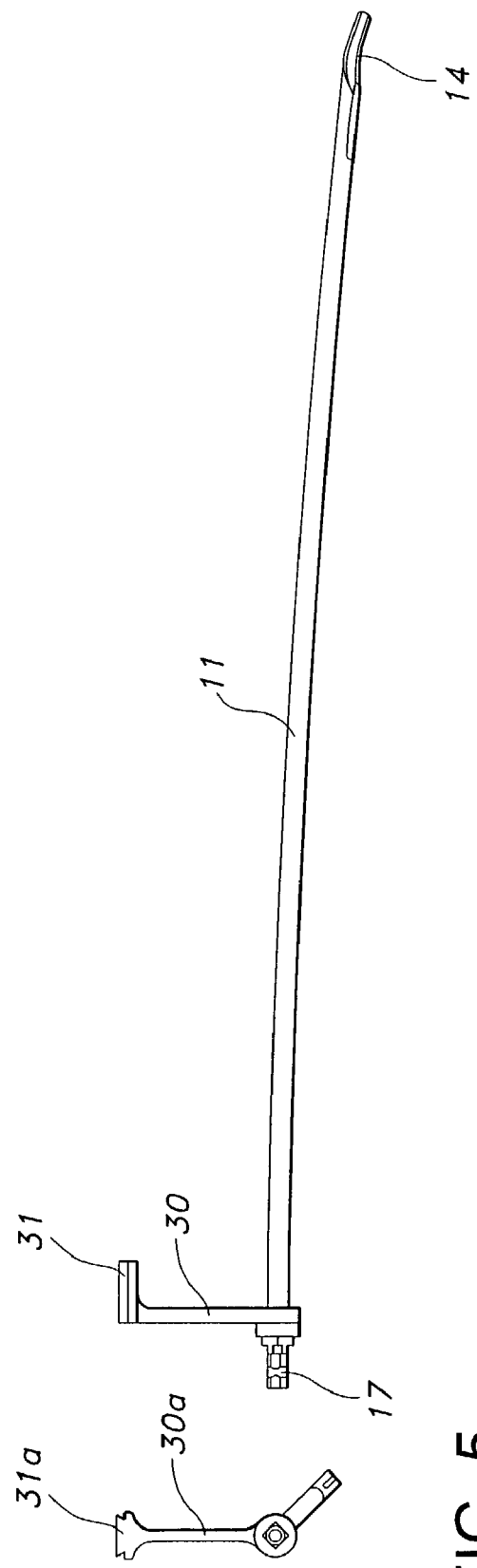
FIG. 4 is an elevation view of an embodiment of a navigated reducer according to certain aspects of the invention.
FIG. 5 is a side elevation view of the navigated reducer of FIG. 4.
Figure 12:
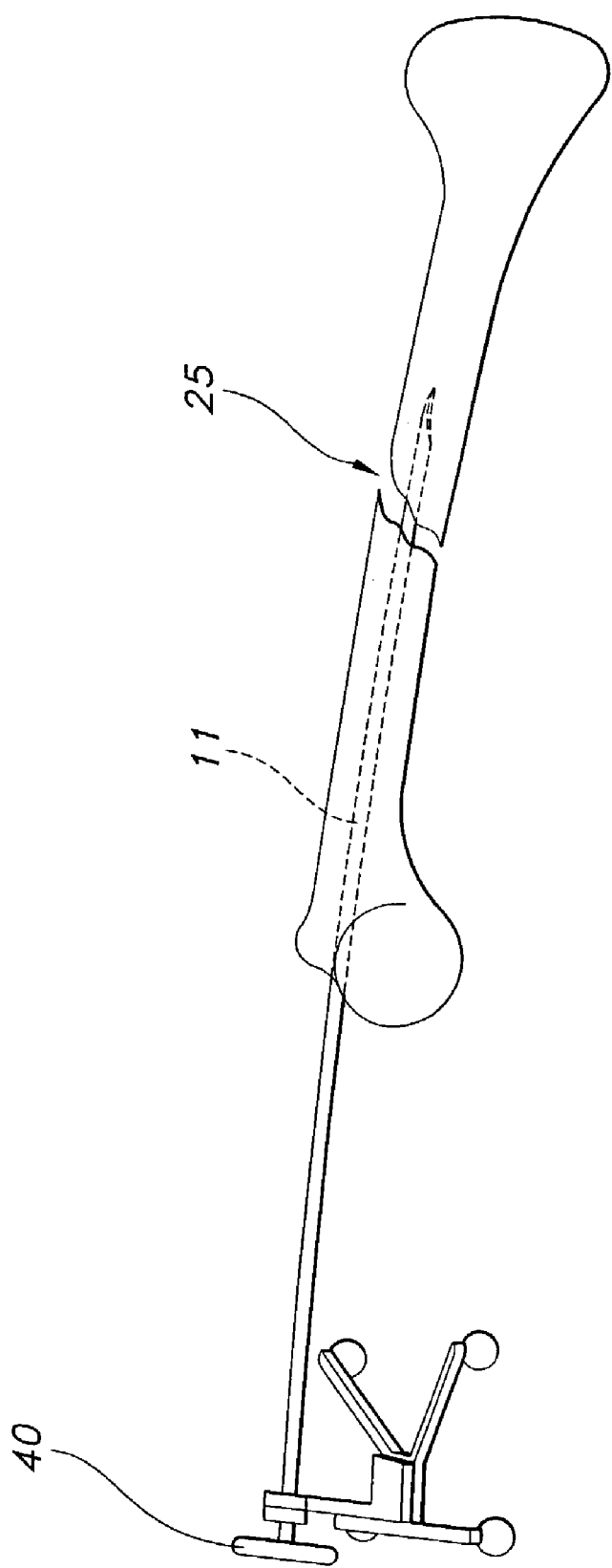
FIG. 12 is an elevation view of an embodiment of a navigated reducer according to certain aspects of the invention being used to reduce a fractured humerus bone.
Figure 13:
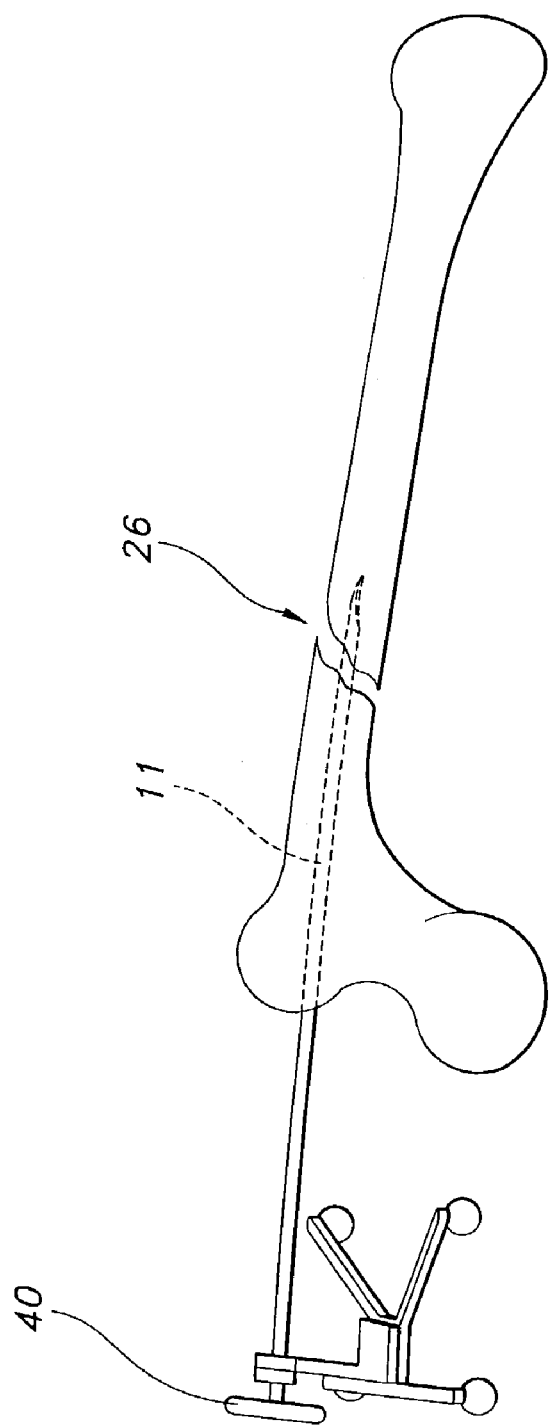
FIG. 13 is an elevation view of an embodiment of a navigated reducer according to certain aspects of the invention being used to reduce a subtrocanteric fracture in a femur.
Figure 14:
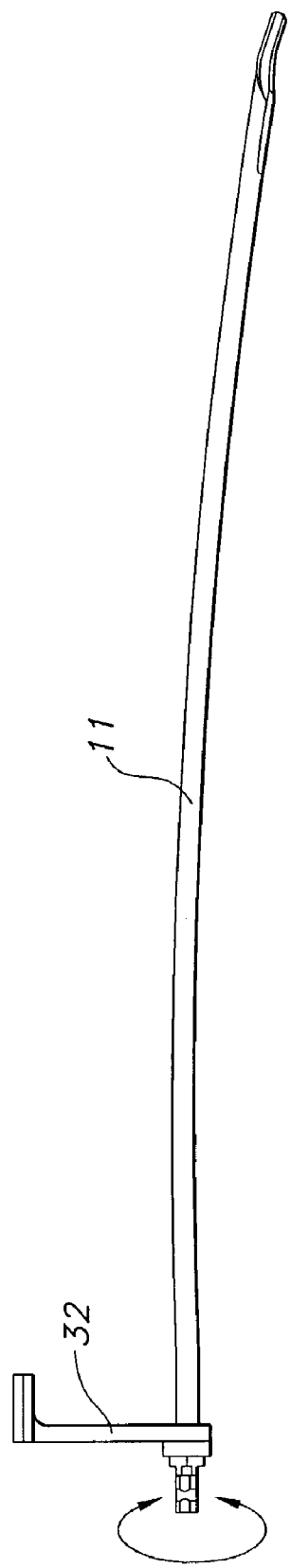
FIG. 14 is an elevation view of an embodiment of a navigated reducer according to certain aspects of the invention with a curved elongated body and an adjustable bracket for supporting a reference.
Figure 15:
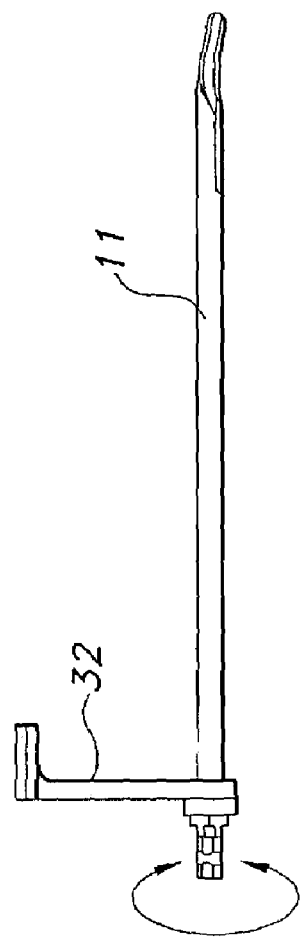
FIG. 15 is an elevation view of an embodiment of a navigated reducer according to certain aspects of the invention with a straight elongated body and an adjustable bracket for supporting a reference.
Figure 16:
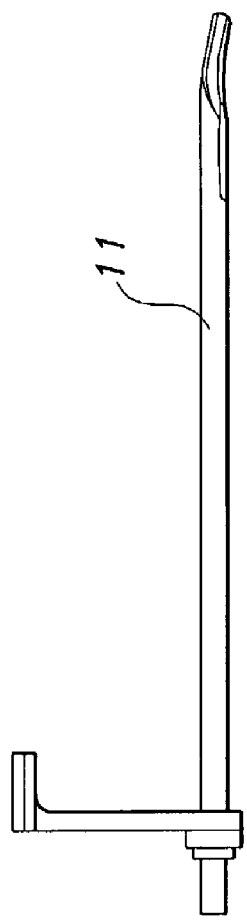
FIG. 16 is an elevation view of an embodiment of a navigated reducer according to certain aspects of the invention with a straight elongated body and a fixed bracket for supporting a reference.

As illustrated in FIG. 2, instrument 10 includes an elongated body 11 and a reference 12 that is coupled to the elongated body 11. FIG. 4 shows elongated body 11 in one embodiment of the invention. As shown, the elongated body 11 is tubular or in similar terminology, cannulated. In other embodiments, the elongated body 11 may be solid. FIGS. 2 and 12 illustrate an elongated body 11 greater than half the greatest length of the fractured bone 25. In other embodiments such as shown in FIG. 13, the elongated body 11 may be less than or equal to half the greatest length of the fractured femoral bone 26. The condition of being less than or equal to half the greatest length is not limited to association with the femur, but can be with regard to any bone. The elongated body 11 may be curved as shown in FIG. 14 or substantially straight as shown in FIGS. 15 and 16. The elongated body 11 shown in FIGS. 2 and 4 has substantially the same curvature as an implant 21 (for example, the implant shown in FIG. 3). Implant 21 may be used to fix bone segments such as upper portion 16 and lower portion 20 in place. The intramedullary reduction device may be bent to follow the shape of whatever implant is used for fixation: IM nails, IM rods, IM hip screws, etc. This has the benefit of positioning the segments in the same position as the subsequent fixation device. However, less exact bends in the elongated body 11 may also be beneficial.

Figure 8:
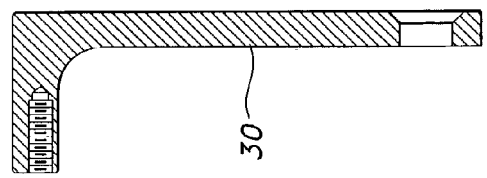
FIG. 8 is a cross-section view taken though the bracket of FIG. 7.
Figure 7:
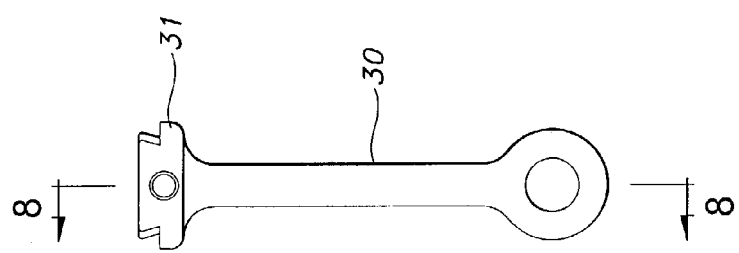
FIG. 7 is a side elevation view of the bracket of FIG. 6.
Figure 22:
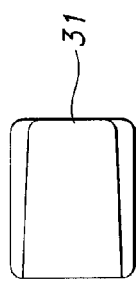
FIG. 22 is a top view of FIG. 6.
Figure 6:
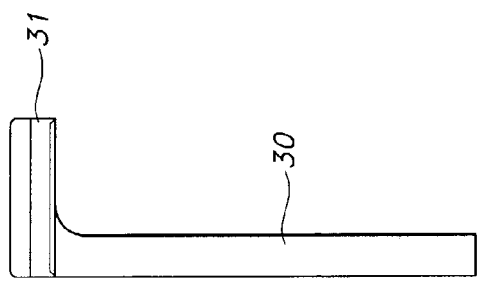
FIG. 6 is an elevation view of a bracket according to certain aspects of the invention used in embodiments of the navigated reducer.
Figure 9:
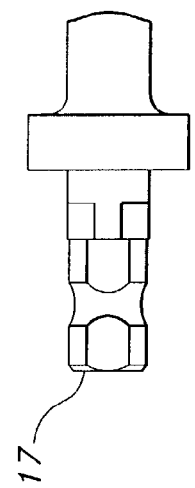
FIG. 9 is an enlarged elevation view of the proximal end of the navigated reducer of FIG. 4.
Figure 11:
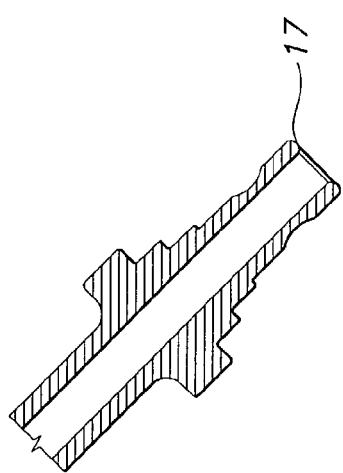
FIG. 11 is a cross-section view taken through the proximal end of FIG. 10.
Figure 10:
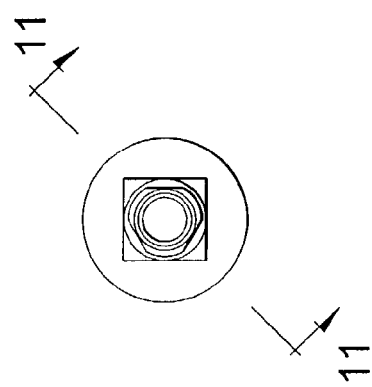
FIG. 10 is a side elevation view of the proximal end of FIG. 9.

The reference 12 enables the instrument 10 to be located by an image-guided surgical navigation system. As illustrated in FIG. 2, reference 12 is coupled to the elongated body 11 in a predefined physical relationship. FIGS. 4–11 show one embodiment of a structure for coupling the reference 12 to the elongated body 11. As illustrated, a bracket 30 is rigidly affixed near a proximal end 17 of the elongated body 11. As best seen in FIGS. 6–8, a dovetail mount 31 is located at one end of the bracket 30. The dovetail mount 31 is designed to be received by a reference 12 that has a mating dovetail opening (not shown).

Bracket 30 is shown as adapted to slide over proximal end 17 of elongated body 11. Although not shown, it is understood that the bracket may alternatively be a clamp that opens and closes to secure elongated body 11 or any other attachment device or structure suitable for attaching components to each other. Those skilled in the art will understand that any member that can rigidly attach reference 12 to instrument 10 is considered a "bracket" within the scope of this invention.

Another embodiment of this invention provides a reference 12 having an integral attachment structure (not shown). Attachment structure may be a bracket integrally formed with reference 12 or any other connection element that will achieve securement of reference 12 to instrument 10.

FIGS. 14 and 15 show articulating brackets 32 releasably movably coupled with elongated body 11. With such a feature, the instrument 10 can be effectively used on either side of the patient by moving the articulating bracket 32 among two or more predetermined positions. In some embodiments, the instrument 10 is releasably movable between positions located at ninety degree intervals around the elongated body. In other words, viewing elongated body from one end, instrument 10 may be positioned at a first ninety degree position, a second ninety degree position, a third ninety degree position, or a fourth ninety degree position.

It is advantageous in some embodiments of the invention to limit the number of positions to which the articulating bracket 32, and thereby the reference 12, may be positioned. This is because a predefined physical relationship must be maintained between the elongated body 11 and the reference 12. By limiting the number of positions, the number of predefined relationships may be more easily defined and tracked.

FIG. 5 illustrates an embodiment of the bracket 30A that is asymmetrically coupled to the elongated body 11. Consequently, if a reference 12 were coupled to the bracket 30A, the reference 12 would also be asymmetrically fixed relative to the elongated body 11. Such an arrangement may be beneficial to more effective use on a particular side of a patient and is sometimes preferred. In other instances, a reference may be symmetrically coupled to the elongated body 11. Preferences are typically dictated by the ability of the image-guided surgical navigation system to effectively detect a reference in a particular application. In some embodiments, the system's detector is a line-of-site device.

Figure 17:
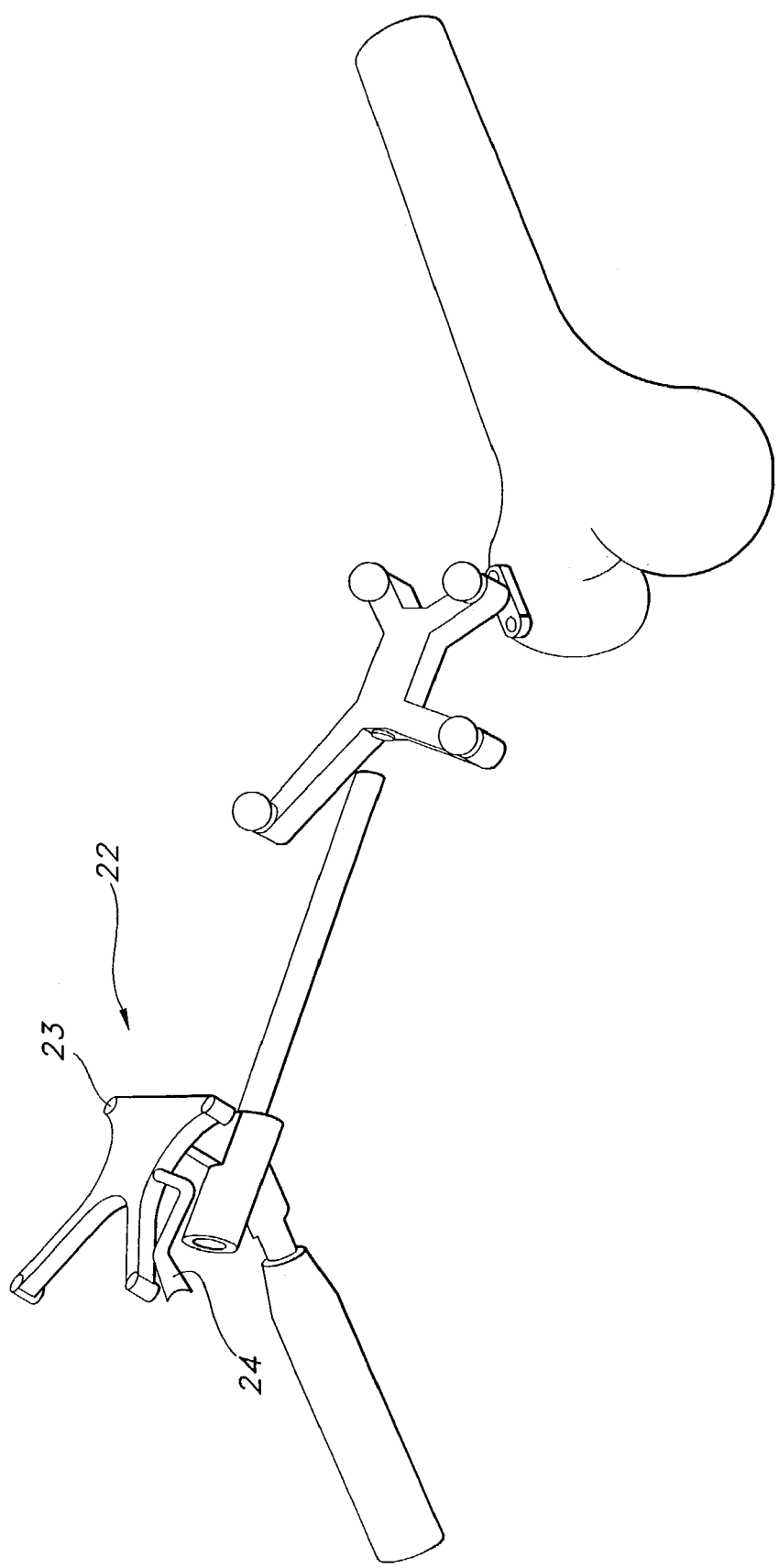
FIG. 17 is a perspective view of an active navigated drill guide and a segment of bone with an attached reference according to certain aspects of the invention.

The reference 12 may also include energy-reflecting surfaces 13 that are detectable by a sensor. FIG. 2 shows four such energy-reflecting surfaces 13 mounted on the reference 12. As illustrated, the energy-reflecting surfaces 13 reflect energy in at least the visible and infrared ranges. However, as discussed in the background section above, various types of energy detectors may be employed. Energy-reflecting surface 13 is considered a passive device because it does not internally generate or convert energy to emit. FIG. 17 illustrates an active energy emitting component 23 that is incorporated into an active reference 22. Note that the active reference 22 includes a wire 24 through which electricity is supplied to the active energy emitting components 23. As shown, there are four active energy emitting components 23. As with the passive device, the active energy emitting components 23 may be operable with various types of energy detectors.

In some embodiments of the invention, the instrument 10 may include a handle 40 (shown in FIGS. 12, 13, 21) connected at proximal end 17. Such a handle 40 would be useful in manipulating the instrument 10 during a surgical procedure. The handle 30 may or may not be removable from instrument 10. If handle 40 is not removable, bracket 30 may be a clamp or other device or structure suitable for attaching components to each other.

Figure 18:
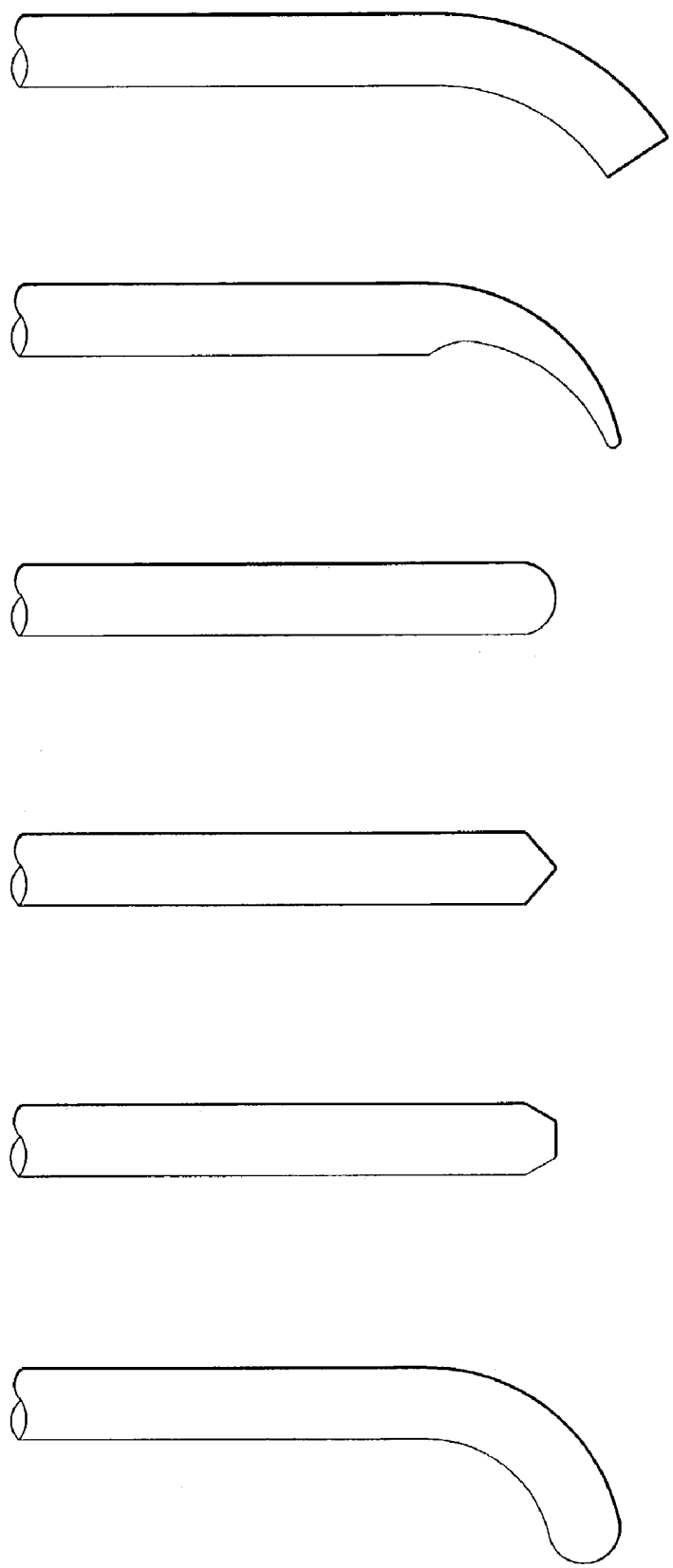
FIG. 18 is an elevational view of various fingers or ends of embodiments of a navigated reducer according to certain aspects of the invention.
Figure 19:
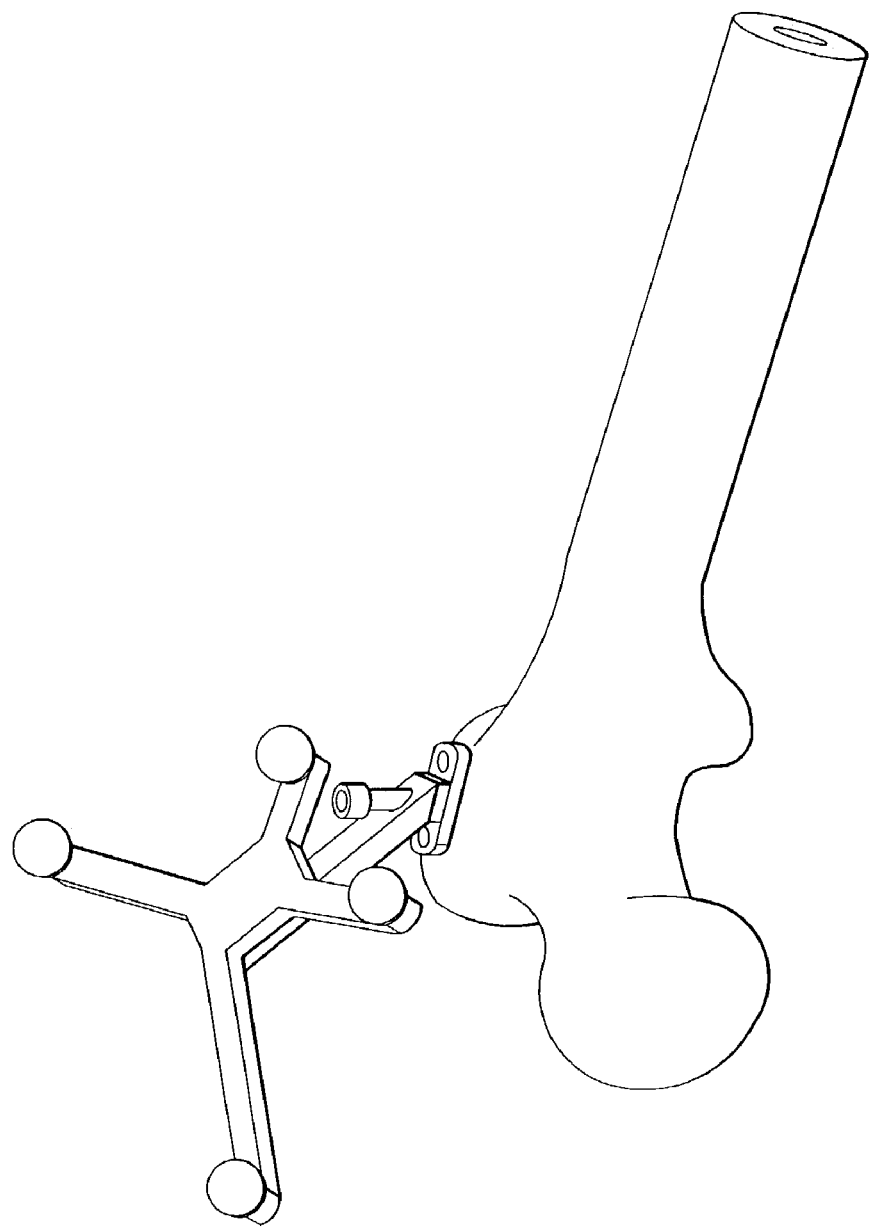
FIG. 19 is a perspective view of a segment of bone with an attached reference according to certain aspects of the invention.
Figure 20:
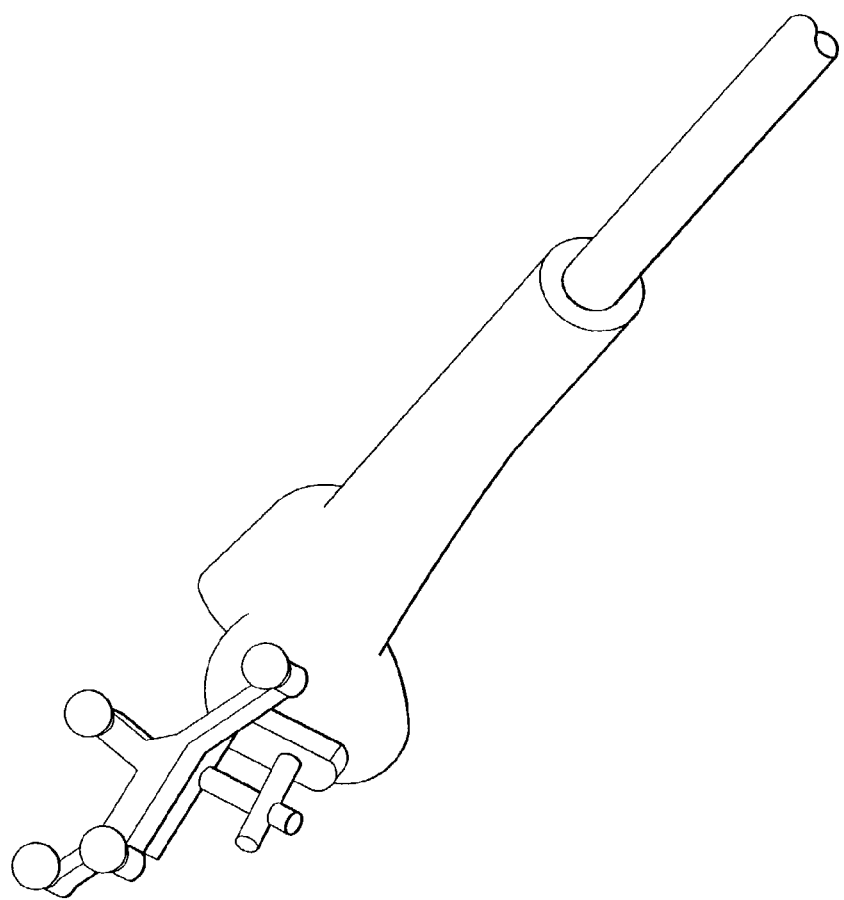
FIG. 20 is a perspective view of a segment of bone with an attached reference according to certain aspects of the invention, where the segment of bone contains an intramedullary nail.

Some embodiments of the invention also include a finger 14, shown for example in FIG. 4. FIG. 18 shows a variety of finger shapes that may also be advantageous in various embodiments of the invention, although different finger shapes may be preferred for various procedures. Note that each of these shapes may be placed on the end of a solid or cannulated elongated body and may themselves be solid or cannulated.

The invention may also be embodied in a system for enabling reduction of a fractured bone. The system is operable to virtually represent at least one fractured segment of the bone and virtually represent an instrument for aligning the at least one fractured segment. The system includes a first reference coupled to the at least one fractured segment, and a second reference coupled to the instrument. The first reference may be coupled to a bone segment through which the instrument is inserted. In this case, position and orientation of another segment of the bone would have to be determined as well, which could be accomplished in any technically effective way.

Alternatively, the first segment could be coupled to a segment of bone toward which the instrument was being directed. In any case, the system also includes a detector operable to collect position and orientation information regarding the at least one fractured segment and the instrument. As discussed in the background section above, the detector could be an infrared camera, visual camera, or any of a variety of sensors capable of detecting any kind of reference or characteristic. The system also includes a data processing device operable to store position and orientation information about one or more fractured segments and the instrument. The data processing device calculates virtual positions of the at least one fractured segment and the instrument based upon inputs from the detector. Such calculations could involve matrix transformations, table look-up functionality, or any other operation effective in calculating the respective virtual positions. An indicator device for notifying a user of the relative positions of the at least on fractured segment and the instrument is also provided. Such an indicator could be a visual cue on a computer screen such as color changes or alignment of articulating lines, sounds, flashes of light, or any device for showing a changeable condition, or some combination of any of these.

Another embodiment of the invention is a method of aligning segments of a fractured bone. As shown in FIG. 3, one method includes attaching a first reference, such as a distal reference 18, to a first segment of a fractured bone, such as a lower portion 20. The position and orientation of distal reference 18 may then be recorded relative to a first datum. As used herein, the term "recording" includes without limitation capturing or storing in computer memory or on a tangible medium such as film. Any such acquisition of information associated with position or orientation, regardless of how transiently maintained in a system, medium, or component is within the definition of recording as used herein. In some embodiments of the invention, recording may include the use of an infrared camera that registers the positions of energy-reflecting surfaces 13.

Alternatively, a reference may not be coupled with a segment of bone, but may be attached to a probe. Such a probe may be recorded at a predetermined anatomical position and orientation. Therefore, by knowing the position of the reference attached to the probe, and the probe's position and orientation on the anatomy, the position of the anatomy can be calculated. In either case, a position and orientation of the first segment of the bone relative to a second datum is recorded. Such a recording may be accomplished by capturing fluoroscopic images of the first segment. As discussed in the background section, the imaging may be through processes other than fluoroscopic imaging, such as CT, MRI, or other effective technologies. The first datum may be the same as the second datum, or information relating the first datum and the second datum may be stored such that transforms relating their relative positions may be calculated. As a result, the first segment will be located relative to the first reference.

The term "datum" as used herein is generally a coordinate system to which three-dimensional association can be made. As such, a number of datums can be defined and then associated to one another by use of three-dimensional transforms, matrix calculations, or the like. Such calculations are well-suited to implementation on computing devices. Similarly, objects being tracked can be positioned and oriented relative to a single datum. In any case, to effectively track objects' positions and orientations, association among the objects must be established and maintained. A strength of the current system is that sensor or camera positions and orientations and patient and instrument positions and orientations may change relative to one another, but through the tracking that embodiments of the invention provide, accurate location and bone segment alignment can be accomplished.

As shown in FIG. 2, a second reference, such as bone reference 15, may be attached to a second segment, such as upper portion 16. As with the first segment and reference, the positions and orientations of the second reference and the second segment are recorded relative to respective third and fourth datums, and the second segment is located relative to the second reference.

A third reference is attached to an instrument 10, such as a reducer. As described above, the reducer is operable to align segments of a fractured bone through the medullary canal of the segments. The term "reducer" as used herein may refer more generally to any instrument used to assist with the alignment of bones. As with the first and second references, a position and orientation of the third reference relative to a fifth datum is recorded. In the case of a reducer or other instrument, locating the reducer relative to the third reference is simplified because there is a predetermined relationship between the reducer and the third reference. As discussed in association with the bracket 30, a single or at least finite number of predetermined relationships between portions of the instrument and the associated reference may be defined. Given a predetermined setting of the instrument relative to the reference, tracking of the reference is effective to track the instrument. Recording of the third reference position and orientation may be accomplished inter-operatively or prior to the beginning of an operation.

Once all of the references, segments, and instrument (or instruments) have been located, they may all be continuously or intermittently tracked without the use of fluoroscopy for as long as desired. As used herein, "continuously" shall mean at a rate that appears substantially continuous to a user, but could include tracking accomplished at a standard electronic sampling rate such as a rate greater than one sample per second. Typically, this tracking is accomplished by use of a computer system that is interfaced with an infrared camera or other device, the computer also calculating transforms regarding each datum and its relationship to each other datum.

Insertion of the instrument 10 may be accomplished prior to, during, or after the process of recording and locating described above. With each of the first segment, the second segment, and the reducer being tracked, the reducer can be aligned with a representation of the second segment. For instance, a surgeon could hold and manipulate a first segment of fractured bone with an inserted reducer while observing a representation of the second segment on a computer screen. The image on the computer screen may also include representations of other bone segments or instruments, such as the reducer. When an indication is received that alignment has been achieved, the surgeon inserts the reducer into the medullary canal of the second segment. The upper portion 16 of a femur shown in FIG. 2 and the lower portion 20 of a femur shown in FIG. 3 are merely examples of the first and second segments.

As previously discussed, the fractured bone need not be a femur. Additionally, the first and second segments may be either the lower or upper portions of bone, depending upon surgeon preference. In many orthopedic procedures, entry can be made from two or more possible approaches.

In some embodiments of the invention, a representation of alignment may include only a representation that the first segment and the second segment, each of which is being tracked, are aligned. In other embodiments, the key to a representation of alignment may be the reducer that is being tracked.

In some embodiments of the invention, only two of a first segment, a second segment, and an instrument may need to be recorded, located, and tracked. For example, if two segments are being tracked, alignment of those segments could be indicated to the user. Given the fact that the user knows that the reducer is located in the medullary canal of one of the segments, the user would know that the reducer could be pushed into the medullary canal of the other segment. Similarly, if only the reducer and the segment into which the reducer is to be inserted second are being tracked, the locations of only that second segment and the reducer could be represented to the user. In this embodiment, the reducer is located in the medullary canal of the other segment. Therefore, by aligning the reducer with the segment into which the reducer is to be inserted second, the user has adequate information to accurately complete the procedure.

Figure 21:
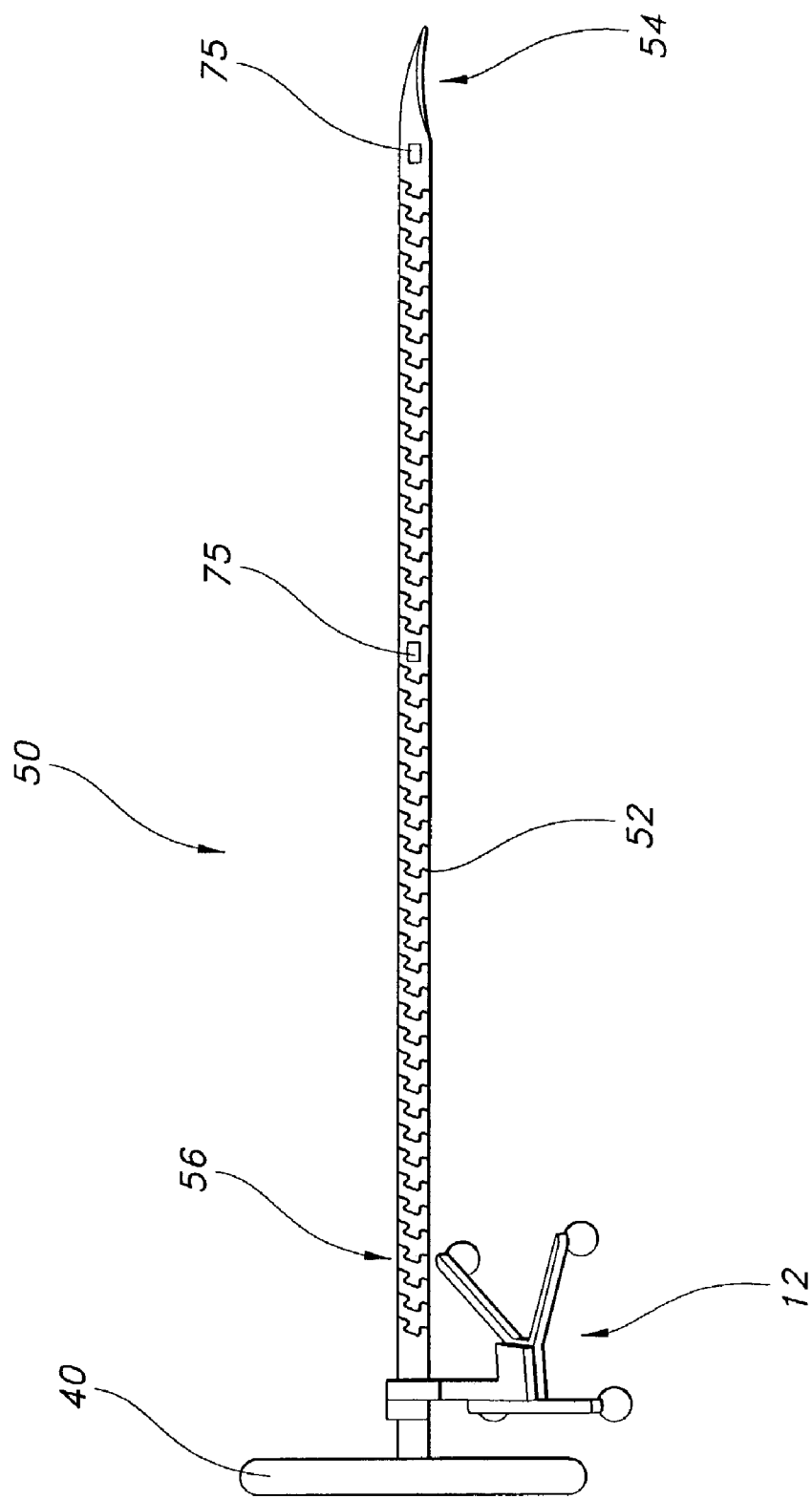
FIG. 21 is a plan view of an at least partially flexible reducer according to certain aspects of the invention with location elements positioned on the elongated body.

In other embodiments and for some procedures, an at least partially flexible reducer 50, as shown in FIG. 21, may be beneficial. For instance, a surgeon may desire to use a flexible reducer if the bone fracture to be aligned or reduced is so misaligned that a rigid reducer is not workable or would be particularly difficult to use. For example, two bone segments of a fracture may be so offset from one another that a rigid reducer would not appropriately engage the second segment. In these instances, the at least partially flexible reducer 50 of the present invention could be used. (For the purposes of this document, "at least partially flexible" and "flexible" mean capable of being even slightly flexed or bent, turned, bowed, or twisted, without breaking; or pliable; or yielding to pressure, whether strong pressure or slight pressure.) The flexible reducer 50 is at least partially flexible to allow the surgeon to more easily manipulate the flexible reducer 50 in order to properly guide it into the second segment. It should be understood that there may be other instances in which a flexible reduced 50 may be preferred.

Flexible reducer 50 according to the particular embodiment shown in FIG. 21 features an at least partially flexible elongated portion or shaft 52. The at least partial flexibility may be provided by a shaft that is hollow, cannulated, or solid. The shaft may have a spiral or helical configuration, a laser cut shaft, a shaft of a material that becomes flexible when subjected to heat (for example, nitinol), a shaft of a thin material that permits flexibility, a shaft with a plurality of flexible elements joined by a connection, a shaft having a series of inter-engaged links, a shaft with a plurality of slots (provided in any configuration) cut at an angle relative to the shaft, a plastic tube (or any other material that provides at least partial elasticity), or any other design that provides a reducer of a flexible nature. Examples of flexible shafts are provided in U.S. Pat. No. 6,053,922, which is incorporated herein by this reference.

Once flexible reducer 50 has been positioned with respect to both bone segments, the surgeon may wish to impart at least partial rigidity to the flexible reducer 50 in order to more properly align the bone segments. In this instance, flexible reducer 50 can be provided with a separate rigid member (not shown), a feature or features on the flexible reducer 50 itself that imparts rigidity to the flexible reducer (also not shown), or any structure or mechanism that imparts at least partial rigidity to reducer 50.

For example, the flexible reducer 50 may be provided with a rigid member with an outer diameter smaller than the inner diameter of the flexible reducer 50, such that inserting the rigid member through the flexible reducer adds rigidity at the desired point in the procedure. Alternatively, the flexible reducer 50 itself can be provided with a cable or wire disposed through the flexible reducer 50 such that when the cable or wire is pulled taut, the flexible shaft 52 is forced to undertake at least partial rigidity. Flexible reducer 50 may alternatively be provided with a trigger, such that once the trigger is activated, the flexible portions become rigid. The flexible portions may be made rigid by a magnetic force, by a mechanical force, or any other mechanism that imparts at least partial rigidity to the flexible reducer 50 at a specified time during the surgery. It should be understood that any feature that provides an at least partially flexible reducer 50 with at least partial rigidity is considered a feature that imparts at least partial rigidity to the reducer within the scope of this invention.

One challenge presented with the use of a flexible reducer 50 is the fact that, by its very nature, it is flexible, and thus, does not retain a rigid position from tip 54 to end 56 in relation to reference 12. This presents a challenge to the use of the image-guided systems and methods described herein, because the flexible elongated portion 52 will not necessarily remain in a fixed position with respect to the reference 12 (or any other reference point being used, such as a bone segment, another instrument, a surgical table, etc.) in order to provide the surgeon with accurate cues about its physical position. Thus, there is also a need to provide a way to determine the position of the flexible elongated portion 52 when it is flexed in a particular direction.

Flexible reducer 50 is consequently provided with one or more location elements 75. One or more location elements 75 assist the determination of at least portions of the physical relationship of the flexible elongated portion 52 with respect to reference 12. A location element 75 may be provided at or near the tip 54 of flexible elongated portion 52, at or near the middle of flexible elongated portion 52, at multiple positions along the flexible elongated portion 52, or any combination of these positions. The location elements may be spaced as close together or as far apart as necessary. The more location elements 75 provided, the more trackability is provided to flexible elongated portion 52.

Location element 75 may be any component or device that permits the physical position of flexible elongated portion 52 to be sensed, detected, imaged, or mapped with respect to reference 12. For example, location elements 75 may be sensed actively or passively by one or more of the following methods: infrared, visual, reflective, sound, ultrasound, radio waves, mechanical waves, magnetic, electromagnetic, electrical, x-ray, GPS systems or chips, transponder, transducer, or any other desired technique. This list is not intended to be inclusive, and any way in which the location of flexible elongated portion 52 can be relayed to a component that can track, sense, image, or map flexible elongated portion 52 for the surgeon to view is considered within the scope of this invention. It should be understood, however, that the flexible elongated portion 52 will be positioned within patient tissue in use, so the location method chosen should be able to sense location element 75 through various tissues, such as bone, muscle, blood, and skin.

Location elements 75 are preferably configured to sense, track, image, and map the physical position of reducer 50 in any plane, location, and/or orientation. In other words, in addition to sensing and tracking the medial-to-lateral movement of flexible reducer 50, location elements 75 are also preferably adapted to sense and track anterior-to-posterior movement.

Location elements may be provided in any configuration or any shape. It is possible for location elements 75 to sense 2-dimensional movement for a rough view of the reducer's location and orientation. In other aspects of the invention, the location elements 75 sense 3-dimensional movement and provide a finer ability to sense and track the location and orientation of reducer 50. Location elements 75 may be provided in any shape or configuration, such as the square-like elements 75 shown in FIG. 21, oval or round-like elements, cross-shaped elements, band-shaped elements, indented elements, bead-shaped elements, and so forth.

Location elements may be located along only one side of flexible elongated portion 52, wrapped around elongated portion 52, positioned in specific increments from one another, or scattered in various, unequal positions about elongated portion 52. As previously mentioned, embodiments according to various aspects of this invention may include only a single location element 75.

A single location element 75 may be used to track and sense the location and orientation of elongated portion 52 with respect to reference 12. To the extent that any other reference point is being used, such as another instrument, a bone segment, or another reference point, it is preferred that two or more location elements 75 be provided.

Location elements 75 may operate in conjunction with systems which are preferably connected to other systems according to various aspects of the invention which sense and track references 12, body portions, instruments, components of other devices, and so forth.

Embodiments of the invention are directed toward enabling reduction of a fractured bone by virtually representing at least one fractured segment of the bone and virtually representing an instrument for aligning two or more segments of bone. As described above, positions and orientations of a segment of bone and an instrument may be recorded and tracked in three-dimensional space with the use of cameras or sensors, imaging devices, and a digital computer. Then, through the use of a sound, visualization, or other stimulation, an indication that alignment has been achieved is provided to a user. Alternatively or in addition, indications regarding the progress of alignment may be provided to the user. "Tracking" as defined for use in this embodiment can include both detecting distinguishing characteristics, such as references or instrument configurations, and processing information regarding changes in position and orientation.

Therefore, embodiments of the invention provide for the location and tracking of bone segments and instruments such that the instruments may be aligned to assist with fixation or therapy. This is accomplished with reduced numbers of x-ray, fluoroscopic, and other such energy-intense imaging devices. There is no requirement for pre-operative imaging or any surgical procedures prior to the primary procedure. With various embodiments of the invention, continuous or nearly continuous monitoring of bone segment and instrument positions is accomplished. Therefore, rapid alignment of bone segments and instruments is facilitated using images of at least one of the bone segments in combination with images of one or more implements, instruments, trials, guide wires, nails, reducers, other surgically related items, or other bone segments which are properly positioned and oriented in the images.

What is claimed is:

1. A method of aligning segments of a fractured bone, comprising:
    attaching a first reference to a first segment of a fractured bone;
    recording a position and orientation of the first reference relative to a first datum;
    recording a position and orientation of the first segment relative to a second datum;
    locating the first segment relative to the first reference;
    attaching a second reference to a second segment of a fractured bone;
    recording a position and orientation of the second reference relative to a third datum;
    recording a position and orientation of the second segment relative to a fourth datum;
    locating the second segment relative to the second reference;
    attaching a third reference to a reducer operable to align segments of a fractured bone;
    recording a position and orientation of the third reference relative to a fifth datum;
    locating the reducer relative to the third reference;
    inserting the reducer into a medullary canal of the first segment;
    aligning the reducer with a representation of the second segment; and
    inserting the reducer into a medullary canal of the second segment, wherein the reducer is used to assist aligning the segments of the fractured bone.

2. The method of claim 1, wherein the recording a position and orientation of the first reference comprises viewing the first reference with an infrared camera.

3. The method of claim 1, wherein the recording a position and orientation of the first segment comprises capturing a fluoroscopic image of the first segment.

4. The method of claim 1, wherein the locating the first segment relative to the first reference comprises continuously tracking the first reference until the reducer is aligned.

5. The method of claim 1, wherein the recording a position and orientation of the second reference comprises viewing the second reference with an infrared camera.

6. The method of claim 1, wherein the recording a position and orientation of the second segment comprises capturing a fluoroscopic image of the second segment.

7. The method of claim 1, wherein the locating the second segment relative to the second reference comprises continuously tracking the second reference until the reducer is aligned.

8. The method of claim 1, wherein the first datum, second datum, third datum, fourth datum, and fifth datum are a common datum.

9. The method of claim 1, wherein the first datum, second datum, third datum, fourth datum, and fifth datum are related to one another by calculable transforms.

10. The method of claim 1, wherein the recording a position and orientation of the third reference comprises viewing the third reference with an infrared camera.

11. The method of claim 1, wherein the aligning the reducer with a representation of the second segment comprises aligning the second segment relative to the first segment, wherein the reducer is inserted in the first segment.

12. The method of claim 1, wherein the aligning the reducer with a representation of the second segment comprises aligning the reducer relative to the second segment.

13. The method of claim 1, wherein the attaching a third reference to a reducer comprises attaching a third reference to an at least partially flexible reducer.

14. The method of claim 13, wherein the attaching a third reference to a reducer comprises attaching a third reference to at least partially flexible reducer that comprises one or more location elements.

15. The method of claim 14, further comprising:
    recording a position and orientation of the one or more location elements relative to the third reference attached to the at least partially flexible reducer; and
    locating the one or more location elements relative to the third reference.

16. The method of claim 15, further comprising:
    establishing the orientation of the one or more location elements.

17. The method of claim 15, further comprising:
    applying a force to the at least partially flexible reducer in order to impart at least partial rigidity to the reducer.

18. A method of aligning segments of a fractured bone comprising:
    inserting a reducer operable to aligning segments of a fractured bone into a medullary canal of a first segment of fractured bone;
    attaching a reference to a second segment of a fractured bone;
    recording a position and orientation of the reference relative to a first datum.
    recording a position and orientation of the second segment relative to a second datum;
    locating the second segment relative to the reference;
    attaching a reducer reference to the reducer;
    recording a position and orientation of the reducer reference relative to a third datum;
    locating the reducer relative to the reducer reference;
    aligning the reducer with a representation of the second segment; and
    Inserting the reducer into a medullary canal of the second segment,
    wherein the reducer is used to assist aligning the segments of the fractured bone.

19. The method of claim 18, wherein the recording a position and orientation of the reference comprises viewing the reference with an infrared camera.

20. The method of claim 18, wherein the recording a position and orientation of the second segment comprises capturing a fluoroscopic image of the second segment.

21. The method, of claim 18, wherein the locating the second segment relative to the reference comprises continuously tracking the reference until the reducer is aligned.

22. The method of claim 18, wherein the first datum, second datum, and third datum are a common datum.

23. The method of claim 18, wherein the first datum, second datum, and third datum are related to one another by calculable transforms.

24. The method of claim 18, wherein the recording a position and orientation of the reducer reference comprises viewing the reducer reference with an infrared camera.

25. The method of claim 18, wherein the locating the reducer relative to the reducer reference comprises calculating the location based on a predetermined relationship between the reducer and the reducer reference.

26. The method of claim 18, wherein the inserting a reducer operable to align segments of a fractured bone into a medullary canal of a first segment of fractured bone comprises inserting an at least partially flexible reducer.

27. The method of claim 26, wherein the inserting a reducer operable to align segments of a fractured bone into a medullary canal of a first segment of fractured bone comprises inserting an at least partially flexible reducer that comprises one or more location elements.

28. The method of claim 27, further comprising:
recording a position and orientation of the one or more location elements relative to the reducer reference; and
locating the one or more location elements relative to the reducer reference.

29. The method of claim 28, further comprising:
establishing the orientation of the one or more location elements.

30. The method of claim 28, further comprising:
applying a force to the at least partially flexible reducer in order to impart at least partial rigidity to the reducer.

31. A method of aligning segments of a fractured bone, comprising:
inserting a reducer operable to align segments of a fractured bone into a medullary canal of a first segment of fractured bone;
attaching a first reference to the first segment;
recording a position and orientation of the first reference relative to a first datum;
recording a position and orientation of the first segment relative to a second datum;
locating the first segment relative to the first reference;
attaching a second reference to a second segment of a fractured bone;
recording a position and orientation of the second reference relative to a third datum;
recording a position and orientation of the second segment relative to a fourth datum;
locating the second segment relative to the second reference;
aligning the first segment with a representation of the second segment; and
inserting the reducer into a medullary canal of the second segment,
wherein the reducer is used to assist aligning the segments of a fractured bone.

32. The method of claim 31, wherein the recording a position and orientation of the first reference comprises viewing the first reference with an infrared camera.

33. The method of claim 31, wherein the recording a position and orientation of the first segment comprises capturing a fluoroscopic image of the first segment.

34. The method of claim 31, wherein the locating the first segment relative to the first reference comprises continuously tracking the first reference until the first segment is aligned.

35. The method of claim 31, wherein the recording a position and orientation of the second reference comprises viewing the second reference with an Infrared camera.

36. The method of claim 31, wherein the recording a position and orientation of the second segment comprises capturing a fluoroscopic image of the second segment.

37. The method of claim 31, wherein the locating the second segment relative to the second reference comprises continuously tracking the second reference until the first segment is aligned.

38. The method of claim 31, wherein the first datum, second datum, third datum, and fourth datum are a common datum.

39. The method of claim 31, wherein the first datum, second datum, third datum, fourth datum are related to one another by calculable transforms.

40. The method of claim 31, wherein the inserting a reducer operable to align segments of a fractured bone Into a medullary canal of a first segment of fractured bone comprises inserting an at least partially flexible reducer comprising two or more location elements.

41. The method of claim 40, further comprising:
recording a position and orientation of the two or more location elements relative to any specified reference point;
locating the two or more location elements relative to the specified reference point.

42. The method of claim 41, further comprising:
establishing the orientation of the two or more location elements.

43. The method of claim 41, further comprising:
applying a force to the at least partially flexible reducer in order to impart at least partial rigidity to the reducer.

44. A method of aligning segments of a fractured bone comprising:
inserting a reducer operable to align segments of a fractured bone into a medullary canal of a first segment of fractured bone;
attaching a reference to a second segment of a fractured bone;
recording a position and orientation of the reference relative to a first datum;
recording a position and orientation of the second segment relative to a second datum including detecting at least a portion of the second segment through the skin of a patient;
locating the second segment relative to the reference;
attaching a reducer reference to the reducer, recording a position and orientation of the reducer reference relative to a third datum;
locating the reducer relative to the reducer reference;
generating an image that comprises a representation of the second segment and a representation of the reducer;
aligning the reducer with the second segment by viewing the generated image and moving the first segment and the reducer relative to the second segment; and
Inserting the reducer into a medullary canal of the second segment in order to align the segments.

45. A system for aligning segments of a fractured bone, comprising:
- a first reference configured to attach to a first segment of a fractured bone;
- a first datum configured to provide a first relative reference for recording a position and orientation of the first reference;
- a second datum configured to provide a second relative reference for recording a position and orientation of the first segment;
- a second reference configured to attach to a second segment of a fractured bone;
- a third datum configured to provide a third relative reference for recording a position and orientation of the second reference;
- a fourth datum configured to provide a fourth relative reference for recording a position and orientation of the second segment;
- a third reference configured to attach to a reducer operable to align segments of a fractured bone;
- a fifth datum configured to provide a fifth relative reference for recording a position and orientation of the third reference; and
- a data processing device for locating the first segment relative to the first reference, locating the second segment relative to the second reference, and locating the reducer relative to the third reference.

* * * * *